US008337813B2

(12) United States Patent
Schultz Sikma et al.

(10) Patent No.: US 8,337,813 B2
(45) Date of Patent: Dec. 25, 2012

(54) CONTRAST AGENTS

(75) Inventors: Elise A. Schultz Sikma, Bartlett, IL (US); Mohammad Aslam, Nashik (IN); Vinayak P. Dravid, Glenview, IL (US); Thomas J. Meade, Wilmette, IL (US); Bradley D. Ulrich, Chicago, IL (US)

(73) Assignee: Northwestern University, Evanston, IL (US)

( * ) Notice: Subject to any disclaimer, the term of this patent is extended or adjusted under 35 U.S.C. 154(b) by 1032 days.

(21) Appl. No.: 12/210,829

(22) Filed: Sep. 15, 2008

(65) Prior Publication Data
US 2009/0269284 A1    Oct. 29, 2009

Related U.S. Application Data

(60) Provisional application No. 60/972,462, filed on Sep. 14, 2007, provisional application No. 60/972,386, filed on Sep. 14, 2007.

(51) Int. Cl.
*A61B 5/055*    (2006.01)
(52) U.S. Cl. .................. 424/9.34; 424/1.11; 424/1.65; 424/1.69; 424/9.1; 424/9.3
(58) Field of Classification Search .................. 424/1.11, 424/1.65, 9.1, 9.3, 9.32, 9.321, 9.322, 9.323, 424/9.33, 9.34, 9.341, 9.35, 9.351, 9.36, 424/9.361, 9.362, 9.363, 9.364, 9.365, 9.7, 424/1.69
See application file for complete search history.

(56) References Cited

U.S. PATENT DOCUMENTS

| | | | |
|---|---|---|---|
| 4,770,183 A | 9/1988 | Groman | |
| 4,822,594 A | 4/1989 | Gibby | |
| 4,826,673 A | 5/1989 | Dean | |
| 5,010,191 A | 4/1991 | Engelstad | |
| 5,055,288 A | 10/1991 | Lewis | |
| 5,078,986 A | 1/1992 | Bosworth | |
| 5,141,740 A | 8/1992 | Rajagopalan | |
| 5,312,617 A | 5/1994 | Unger | |
| 5,707,605 A | 1/1998 | Meade | |
| 5,846,517 A * | 12/1998 | Unger | 424/9.52 |
| 5,980,862 A | 11/1999 | Meade | |
| 6,461,586 B1 * | 10/2002 | Unger | 424/9.32 |
| 6,656,450 B2 | 12/2003 | Hubin | |
| 6,713,045 B1 | 3/2004 | Meade | |
| 6,713,046 B1 | 3/2004 | Meade | |
| 6,770,261 B2 | 8/2004 | Meade | |
| 7,029,655 B2 | 4/2006 | Allen | |
| 7,354,568 B1 | 4/2008 | Meade | |
| 2002/0151787 A1 | 10/2002 | Bjornerud et al. | |
| 2002/0197648 A1 | 12/2002 | Silva | |
| 2003/0004236 A1 | 1/2003 | Meade | |
| 2003/0021750 A1 | 1/2003 | Bakan | |
| 2003/0120151 A1 | 6/2003 | Constantinides | |
| 2003/0135108 A1 | 7/2003 | Silva | |
| 2003/0198597 A1 | 10/2003 | Meade | |
| 2004/0170563 A1 | 9/2004 | Meade | |
| 2005/0002866 A1 | 1/2005 | Meade | |
| 2005/0220714 A1 | 10/2005 | Kauzlarich et al. | |
| 2006/0078502 A1 | 4/2006 | Dewanjee | |
| 2006/0088475 A1 | 4/2006 | Duimstra | |

OTHER PUBLICATIONS

Barletta et al. "Inhibition of pseudomonal ulceration in rabbit corneas by a synthetic matrix metalloproteinase inhibitor" 1996 Invest Ophthalmol Vis. Sci. 37, 20-28.
Bauer et al., "Carboxyamido-triazole inhibits angiogenesis by blocking the calcium-mediated nitric-oxide synthase-vascular endothelial growth factor pathway" 2000 J. Pharmacology & Experimental Therapeutics 292(1):31-7.
Buchardt et al. Chem. Eur. J. 5, 2877-2884 (2000).
Bulte et al. "T1 and T2 relaxometry of monocrystalline iron oxide nanoparticles (MION-46L): theory and experiment" 1998 Acad. Radiol. 5 (suppl 1), S137-S140.
Caravan et al., "Gadolinium(III) Chelates as MRI Contrast Agents: Structure, Dynamics, and Applications" Chem. Rev. 1999, 99, 2293-2352.
Charoenrat et al. Int. J. Cancer 86, 307-317 (2000).
Codony-Serat et al., Cancer Res. 59:1196 (1999).
Coussens et al., "Matrix metalloproteinase inhibitors and cancer: trials and tribulations" Science 2002, 295:2387-2392.
Cramer et al., Gastrent. 166 (4 pt 2):pA1116 (G4840) (1999).
Dahlberg et al. "Selective enhancement of collagenase-mediated cleavage of resident type II collagen in cultured osteoarthritic cartilage and arrest with a synthetic inhibitor that spares collagenase 1 (matrix metalloproteinase 1)" 2000 Arthritis Rheum. 43, 673-682.
DEFOTIS Physical Review B 1981, 23, 4714-4740.
Deng et al. Colloids Surf, A 2005, 262, 87-93.
Depowski et al., "Prognostic significance of p34cdc2 cyclin-dependent kinase and MIB1 overexpression, and HER-2/neu gene amplification detected by fluorescence in situ hybridization in breast cancer" 1999 Am. J. Clin. Pathol. 112:459 abstract only.
Duenas et al., "Inhibition of rat corneal angiogenesis by 16-kDa prolactin and by endogenous prolactin-like molecules" 1999 Investigative Ophthalmology 40:2498-505.
Duimstra et al. "A gadolinium chelate for detection of beta-glucuronidase: a self-immolative approach" 2005 J. Am. Chem. Soc. 127, 12847-12855.
Earp et al., Breast Canc. Res. Treat. 35:115 (1995).
Frullano et al., "Multimodal MRI contrast agents" 2007 JBIC 12, 939-949.
Garbett et al. "Proteolysis in colorectal cancer" 1999 Mol. Pathol. 52, 140-145.
Gerion et al. J. Phys. Chem. C 2007, 111, 12542-12551.
Gersh and Catchpole, "The organization of ground substance and basement membrane and its significance in injury njury disease and growth" American Journal of Anatomy 1949, 85:457-521.
Greenwald et al. "In vitro sensitivity of the three mammalian collagenases to tetracycline inhibition: relationship to bone and cartilage degradation" 1998 Bone 22, 33-38.
Hao et al. Exp. Eye Res. 68, 565-572 (1999).
Hao et al. Exp. Eye Res. 69, 595-601 (1999).
Huber "Synthesis, properties, and applications of iron nanoparticles" 2005 Small 1, 482-501.

(Continued)

*Primary Examiner* — D L Jones
(74) *Attorney, Agent, or Firm* — Casimir Jones, S.C.

(57) ABSTRACT

The present invention relates generally to multimodal magnetic resonance imaging (MRI) contrast agents. In particular, the present invention provides a MRI contrast agent configured to manipulate both the longitudinal ($T_1$) and transverse ($T_2$) relaxation times of surrounding water proton spins.

14 Claims, 19 Drawing Sheets

OTHER PUBLICATIONS

Ikeda et al. "Anti-invasive activity of synthetic serine protease inhibitors and its combined effect with a matrix metalloproteinase inhibitor" 1998 Anticancer Res. 18, 4259-4265.
Itoh et al. "Purification and refolding of recombinant human proMMP-7 (pro-matrilysin) expressed in *Escherichia coli* and its characterization" 1996 J. Biochem. 119, 667-673.
Johnson et al., Curr. Opin. Chem. Biol. 2:466 (1999).
Kelly et al., "Seprase, a membrane-bound protease, is overexpressed by invasive ductal carcinoma cells of human breast cancers" 1998 Mod. Path. 11(9):855 abstract only.
Kimura et al., "Expression of human regenerating gene mRNA and its product in normal and neoplastic human pancreas" 1992 Cancer 70:1857.
Kolb et al., J. Neuroimmunol. 84, 143-150 (1998).
Lee et al. "Synthesis and magnetic properties of silica-coated FePt nanocrystals" 2006 J. Phys. Chem. 110, 11160-11166.
Li et al., "Systemic delivery of antiangiogenic adenovirus AdmATF induces liver resistance to metastasis and prolongs survival of mice" 1999 Human Gene Therapy 10(18):3045.
Lien et al. Prostrate 43, 77-82 (2000).
Lin et al. "Effect of Ni and Zn substitution on magnetic properties of the high-Tc superconductor GdBa2Cu3O7-y" 1990 Physical Review B, 42, 2554-2557.
Liu et al. "Paramagnetic particles carried by cell-penetrating peptide tracking of bone marrow mesenchymal stem cells, a research in vitr" 2006 Biochemical and Biophysical Research Communications 347, 133-140.
Lombard et al. "Synthetic matrix metalloproteinase inhibitors and tissue inhibitor of metalloproteinase (TIMP)-2, but not TIMP-1, inhibit shedding of tumor necrosis factor-alpha receptors in a human colon adenocarcinoma (Colo 205) cell line" 1998 Cancer Res. 58, 4001-4007.
Louie et al., "In vivo visualization of gene expression using magnetic resonance imaging" 2000 Nature Biotechnology, 18:321-325.
MacDougall et al. "Contributions of tumor and stromal matrix metalloproteinases to tumor progression, invasion and metastasis" 1995 Cancer and Metastasis Rev. 14:351.
Makela et al. Exp. Cell Res. 251, 67-78 (1999).
Maquoi et al. "Inhibition of matrix metalloproteinase 2 maturation and HT1080 invasiveness by a synthetic furin inhibitor" 1998 FEBS Lett. 424, 262-266.
Maquoi et al. "Membrane type 1 matrix metalloproteinase-associated degradation of tissue inhibitor of metalloproteinase 2 in human tumor cell lines" 2000 J. Biol. Chem. 275, 11368-11378.
Mirelle Gaire et al., "Structure and expression of the human gene for the matrix metalloproteinase matrilysin" 1994 J. Biol. Chem. 269;2032.
Montesano et al. "Constitutively active mitogen-activated protein kinase kinase MEK1 disrupts morphogenesis and induces an invasive phenotype in Madin-Darby canine kidney epithelial cells" 1999 Cell Growth Differ. 10, 317-332.
Nakahara at al., "Transmembrane/cytoplasmic domain-mediated membrane type 1-matrix metalloprotease docking to invadopodia is required for cell invasion" 1997 PNAS USA 94:7959.
Nakashima et al., "Inhibition of cell growth and induction of apoptotic cell death by the human tumor-associated antigen RCAS1" 1999 Nature Med. 5:938.
Nelson et al., "Matrix metalloproteinases: biologic activity and clinical implications" 2000 Journal of Medical Oncology 18:1135-1149.
Netzel-Arnett et al., "Continuously recording fluorescent assays optimized for five human matrix metalloproteinases" 1991 Analytical Biochemistry 195:86-92.
Netzel-Arnett, S., et al., "Comparative sequence specificities of human 72- and 92-kDa gelatinases (type IV collagenases) and PUMP (matrilysin)" 1993 Biochem., 32:6427-6432.

Nicosia et al., "Inhibition of angiogenesis in vitro by Arg-Gly-Asp-containing synthetic peptide" 1991 Am. J. Pathology 138(4):829.
Ohkubo et al. "Identification of substrate sequences for membrane type-1 matrix metalloproteinase using bacteriophage peptide display library" 1999 Biochem. Biophys. Res. Commun. 266, 308-313.
Poulsom et al., "Stromal expression of 72 kda type IV collagenase (MMP-2) and TIMP-2 mRNAs in colorectal neoplasia" 1992 Am. J. Path. 141:389.
Price et al. "Marked inhibition of tumor growth in a malignant glioma tumor model by a novel synthetic matrix metalloproteinase inhibitor AG3340" 1999 Clin. Cancer Res. 5, 845-854.
Rechreche et al., Int. J. Cancer 81:688 (1999).
Santos et al. "Rodent pharmacokinetic and anti-tumor efficacy studies with a series of synthetic inhibitors of matrix metalloproteinases" 1997 Clin Exp. Metastasis 15, 499-508.
Schultz et al. "Treatment of alkali-injured rabbit corneas with a synthetic inhibitor of matrix metalloproteinases" 1992 Invest OphthalmoL Vis. Sci. 33, 3325-33331.
Shackney et al., "Genetic evolutionary staging of early non-small cell lung cancer . . . " 1999 J. Thorac. Cadio. Surg 118:259.
Sipose et al., Annal of the New York Academy of Sciences 732:263 (1994 and references therein).
Song et al. "Synthesis of multimeric MR contrast agents for cellular imaging" J. Am. Chem. Soc. 2008, 130, 6662-6663.
Stack and Gray, "Comparison of vertebrate collagenase and gelatinase using a new fluorogenic substrate peptide" 1989 Journal of Biological Chemistry 264:4277-4281.
Stearns et al., "Type IV collagenase (M(r) 72,000) expression in human prostate: benign and malignant tissue" 1993 Cancer Res. 53:878.
Stetler-Stevenson et al., "Extracellular matrix 6: role of matrix metalloproteinases in tumor invasion and metastasis" 1993 FASEB 7:1434.
Sun et al. "Monodisperse MFe2O4 (M=Fe, Co, Mn) nanoparticles" 2004 J. Am. Chem. Soc. 126, 273-279.
Hansson et al., "Cloning, expression, and characterization of stratum corneum chymotryptic enzyme. A skin-specific human serine proteinase" 1994 J. Biol. Com. 269:19420.
Uzui et al. "The role of protein-tyrosine phosphorylation and gelatinase production in the migration and proliferation of smooth muscle cells" 2000 Atherosclerosis 149, 51-59.
Van Hinsbergh et al., "Angiogenesis and anti-angiogenesis: perspectives for the treatment of solid tumors" 1999 Annals of Oncology 10 Supp. 4:60.
Vestal and Zhang. Int. J. of Nanotechnology 2004, 1, 240-263.
Villunger et al., "The great escape: is immune evasion required for tumor progression?" 1999 Nature Med. 5:874.
Wallace et al. "The matrix metalloproteinase inhibitor BB-1101 prevents experimental autoimmune uveoretinitis (EAU)" 1999 Clin. Exp. Immunol. 118, 364-370.
Wang et al. J. Biol. Chem. 274, 3304333049 (1999).
Werner et al. "Highly soluble tris-hydroxypyridonate Gd(III) complexes with increased hydration number, fast water exchange, slow electronic relaxation, and high relaxivity" J. Am. Chem. Soc. 2007, 129, 1870-1871.
Woods et al. "Paramagnetic lanthanide complexes as PARACEST agents for medical imaging" 2006 Chemical Society Reviews 35, 500-511.
Yang et al. Advanced Materials 2006, 18, 2890-2894.
Yip et al. Invest New Drugs 17, 387-399 (1999).
Zhang et al., "Maspin is an angiogenesis inhibitor" 2000 Nature Medicine 6(2):196.
Zucker and Cao, "Imaging metalloproteinase activity in vivo" 2001 Nature Medicine 7:655-656.

\* cited by examiner

A

B

1. DIPA-SS-pyridyl

2. Gd(III)DIPA-SS-pyridyl

CONTRAST AGENTS

The present application claims priority to U.S. Provisional Patent Application Ser. Nos. 60/972,462 filed Sep. 14, 2007 and 60/972,386 filed Sep. 14, 2007, the entire disclosures of which are herein incorporated by reference in their entireties.

This invention was made with government support under grant numbers 5 U54 CA119341-02, 5 P50 NS054287-02 and 5 RO1 EB005866-02 awarded by the National Institutes of Health, and grant number DMR-0603184/001 awarded by the National Science Foundation. The government has certain rights in the invention.

FIELD OF THE INVENTION

The present invention relates generally to multimodal magnetic resonance imaging (MRI) contrast agents. In particular, the present invention provides a MRI contrast agent configured to manipulate both the longitudinal ($T_1$) and transverse ($T_2$) relaxation times of surrounding water proton spins.

BACKGROUND OF THE INVENTION

Cancer is one of the leading causes of death in the United States, accounting for about 25 percent of all deaths. Since the mid-1970s, the survival rate of cancer on average has increased from about 50 percent to over 60 percent, reflecting improvements in treatment and diagnosis at earlier stages of cancer. However, there are differences in the survival rates of varying types of cancer. More specifically, patients with metastatic cancer have significantly lower odds of survival. For example, the 5-year relative survival for localized breast cancer is about 98 percent today; however, that rate drops to 26 percent for women with metastatic breast cancer (American Cancer Society Cancer Facts & Figures 2007. Atlanta: American Cancer Society; 2007; herein incorporated by reference in its entirety). Thus, the development of new tools for early metastatic cancer detection is critical for improving the odds of survival for many cancer patients. Metastatic tumors have been shown to have elevated levels of enzymes, such as matrix metalloproteinsase-7 (MMP-7), that break down tissues in the body. Since these enzymes are present at high levels, they have the potential to become targets for anticancer imaging and diagnostic techniques.

Matrix metalloproteinases (MMPs) are a family of zinc containing enzymes that mediate the breakdown of connective tissues (Whittaker et al., Chemical Reviews 1999, 99:2735-2776; herein incorporated by reference in its entirety). MMPs are important in many physiological processes including wound healing, bone resorption, and uterine and breast involution (Mullins and Rohrlich, Biochim and Biophys Acta 1983, 695.177-214; herein incorporated by reference in its entirety). The enzymes are generally expressed at low levels, but these levels rise rapidly during inflammation, wound healing, and cancer (Coussens et al., Science 2002, 295:2387-2392; herein incorporated by reference in its entirety). Overexpression of MMPs has been linked to several degenerative diseases such as multiple sclerosis (Rosenberg, et al., Neurology 1996, 46:1626-1632., Chandler, et al., Neuroscience Letter 1995, 201:223-226., Proost et al., Biochemical and Biophysical Research Communications 1993, 192:1175-1181., Gijbels et al., Journal of Cellular Biochemistry (Supplement) 1994, 18D, 143.; herein incorporated by reference in their entireties), corneal ulceration (Hook, et al., Investigative Opthalmology 1973, 12:771-776.; herein incorporated by reference in its entirety), periodontal disease (Golub et al., Journal of the American Dental Association 1994, 125:163-171.; herein incorporated by reference in its entirety), gastrointestinal ulceration (Saarialho-Kere et al., American Journal of Pathology 1996, 148:519-526.; herein incorporated by reference in its entirety), abdominal aortic aneurysm (Thompson et al., Annals of the New York Academy of Sciences 1996, 800: 157-174.; herein incorporated by reference in its entirety), rheumatoid arthritis (Cawston, T E, Pharmacology & Therapeutics 1996, 70:163-182.; herein incorporated by reference in its entirety), osteoarthritis (Cawston, T E, Pharmacology & Therapeutics 1996, 70:163-182., O'Byrne et al., Inflammation Research 1995, 44:S 117-S118; herein incorporated by reference in their entireties), cancer invasion (Edwards and Murphy, Nature 1998, 394:527-528., Kataoka et al., American Journal of Pathology 1999, 154:457-468., Brabletz et al., American Journal of Pathology 1999, 155:1033-1038., Noe et al., Cell Science 2001, 114:111-118.; herein incorporated by reference in their entireties), and tumor metastasis (Aparicio et al., Carcinogenesis 1999, 20:1445-1451., Lampert et al., American Journal of Pathology 1998, 153:429-437., Zucker et al., American Journal of Pathology 2001, 158:1921-1928., Zeng et al., Clinical Cancel Research 2002, 8:144-148., Chambers et al., Journal of the National Cancer Institute 1997, 89:1260-1270.; herein incorporated by reference in their entireties). As early as 1949 MMPs were recognized as depolymerizing enzymes that were believed to facilitate tumor growth by degrading connective tissues (Gersh and Catchpole, American Journal of Anatomy 1949, 85:457-521.; herein incorporated by reference in its entirety). Recently, the mechanistic role of MMPs in tumor metastasis and invasion has been shown to be much more complex than previously thought. However, the positive correlation between MMP expression levels and the invasive potential of a tumor remains. The detection of MMP is critical for identifying metastatic cancer and could be used to monitor the efficacy of MMP inhibitors, leading to the optimization of anti-cancer therapeutic protocols (Zucker and Cao, Nature Medicine 2001, 7:655-656., Coussens et al., Science 2002, 295:2387-2392., Nelson et al., Journal of Medical Oncology 2000, 18:1135-1149.; herein incorporated by reference in their entireties). The current method of monitoring MMP activity consists of ex vivo assays on excised tissues or fluid samples. In order to detect MMP activity in vitro, fluorescent probes have been developed including ultraviolet-visible and near-infrared probes and proteolytic beacons (Stack and Gray, Journal of Biological Chemistry 1989, 264:4277-4281., Netzel-Arnett et al., Analytical Biochemistry 1991, 195:86-92.; herein incorporated by reference in their entireties). The practical applications of fluorescence techniques are restricted to the observation of cells, small animals, and tumors near the surface of the skin due to the limited penetration of light (<10 mm). Thus, there has been a need to develop techniques for MMP detection that are more applicable to humans (Coussens et al., Science 2002, 295:2387-92., Nelson et al., Journal of Clinical Oncology 2000, 18:1135-1149.; herein incorporated by reference in their entireties). MRI provides an alternative to light microscopy, allowing the noninvasive, in vivo imaging of opaque organisms in three dimensions at millimeter resolution (Louie et al., Nature Biotechnology 2000, 18:321-325.; herein incorporated by reference in its entirety).

MRI has become a popular technique for noninvasive imaging of opaque specimens due to its high spatial and temporal resolution. In MRI, images are acquired by employing radio frequency pulses to excite nuclear spins of a specimen. The observed signal is from the protons of water molecules in the specimen. MRI generates 3-D images due to intrinsic variations in water proton concentrations in different tissues. Whereas optical microscopy is limited by light scattering, MRI can image in three dimensions with high spatial and temporal resolution. Exogenous agents can be used manipulate relaxation times ($T_1$ and/or $T_2$) of water protons within a sample and enhance contrast in the image. Principle limitations to current agents are amplification of signal, in vivo delivery, lack of multimodal validation, and the absence of biochemical reporters. Improved systems are needed to expand imaging capabilities.

SUMMARY

The present invention relates generally to multimodal magnetic resonance imaging (MRI) contrast agents. In particular, the present invention provides MRI contrast agents configured to manipulate both the longitudinal ($T_1$) and transverse ($T_2$) relaxation times of surrounding water proton spins. In some embodiments, the contrast agents comprise one or more enzymatically cleavable linkers. In some embodiments, the present invention relates to a contrast agent useful in detecting enzyme activity in vivo.

In some embodiments, the present invention provides a magnetic resonance contrast agent composition comprising one or more $T_1$ contrast agent portions, one or more $T_2$ contrast agent portions, and one or more linker regions. In some embodiments, the $T_1$ contrast agent portion comprises a paramagnetic metal ion chelate. In some embodiments, the metal ion chelate comprises a paramagnetic metal ion (e.g. Gd(III)). In some embodiments, the $T_1$ contrast agent portion of the present invention is configured to provide reduction in $T_1$ relaxation time. In some embodiments, the $T_2$ contrast agent portion of the present invention comprises a superparamagnetic nanoparticle. In some embodiments, the $T_2$ contrast agent portion of the present invention is configured to provide a reduction in $T_2$ relaxation time. In some embodiments, the $T_2$ contrast agent portion of the present invention is configured to provide a reduction in $T_2$ and $T_1$ relaxation times.

In some embodiments of the present invention, the linker region is a cleavable linker region. In some embodiments, the cleavable linker region comprises a peptide linker portion. In some embodiments, the cleavable linker region is configured to undergo enzymatic cleavage. In some embodiments, the enzymatic cleavage comprises proteolysis. In some embodiments of the present invention, the peptide linker portion comprises a MMP-7 peptide linker. In some embodiments, the MMP-7 peptide linker is cleavable by the MMP-7 enzyme.

In some embodiments, the linker region of the present invention connects one said $T_1$ contrast agent portion to one said $T_2$ contrast agent. In some embodiments, a $T_2$ contrast agent portion is connected to more than one $T_1$-relaxation contrast agent portions by multiple linkers. In some embodiments, more than one $T_2$ contrast agent portions are connected to more than one $T_1$ contrast agent portions by multiple linkers.

In some embodiments, the present invention provides a magnetic resonance contrast agent composition comprising one or more $T_1$ contrast agent portions, one or more $T_2$ contrast agent portions, and one or more linker regions; further providing an additional functional portion. In some embodiments, the additional functional portion is an imaging tag. In some embodiments, the present invention provides an optical imaging tag. In some embodiments, the present invention provides an additional targeting moiety.

In some embodiments, the present invention provides pharmaceutical formulation comprising a contrast agent of a magnetic resonance contrast agent composition comprising one or more $T_1$ contrast agent portions, one or more $T_2$ contrast agent portions, and one or more linker regions, and a pharmaceutically acceptable carrier, wherein the formulation is suitable for administration as an imaging enhancing agent and the contrast agent is present in an amount sufficient to enhance a magnetic resonance image.

BRIEF DESCRIPTION OF THE DRAWINGS

The foregoing summary and detailed description is better understood when read in conjunction with the accompanying drawings which are included by way of example and not by way of limitation.

DEFINITIONS

Figure 1:
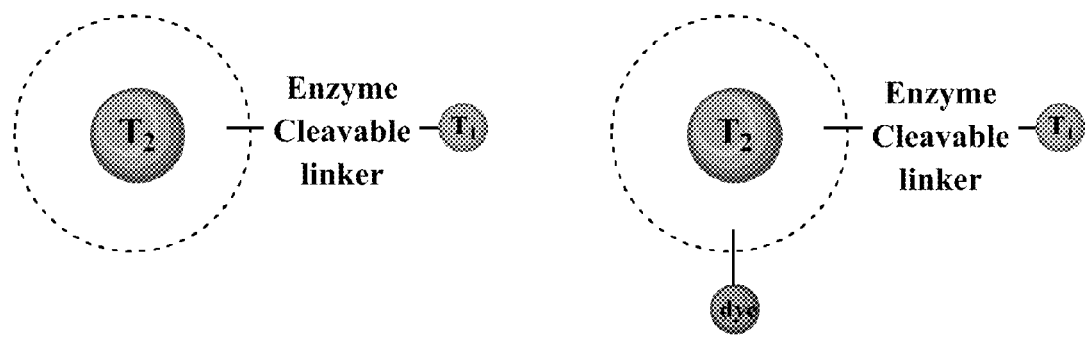
FIG. 1 shows: A) the basic design of enzyme-activated $T_1$-$T_2$ multimodal contrast agent for MRI: left: enzyme-activated $T_1$-$T_2$ agent; right: $T_1$-$T_2$ agent with added optical dye. B) an illustration of general activation of enzyme $T_1$-$T_2$ contrast agent via cleavage of an enzyme cleavable linker.
Figure 1:
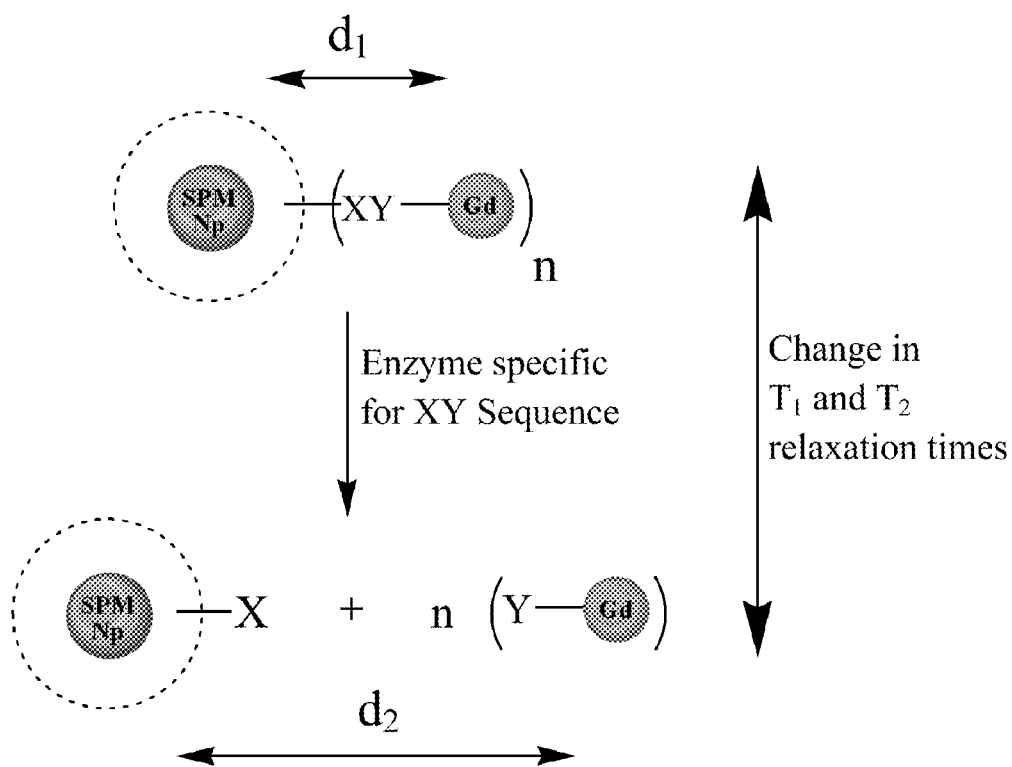

The term "bioactive molecule" refers to any chemical entity, whether in the solid, liquid, or gaseous phase which is capable of providing a biological effect when administered to a subject in accordance with the invention. The term "bioactive molecule" includes synthetic compounds, natural products and macromolecular entities such as polypeptides, polynucleotides, or lipids and also small entities such as neurotransmitters, ligands, hormones or elemental compounds. The term also includes such compounds whether in a crude mixture or purified and isolated.

As used herein, the term "relaxation time" refers to the time required for a nucleus which has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and $T_2$. $T_1$ is referred to as the longitudinal relaxation time and $T_2$ is referred to as the transverse relaxation time. Other relaxation times of relevance include, but are not limited to $T_1\rho$ (the paramagnetic contribution to the longitudinal relaxation rate) and $T_2^*$ (the transverse relaxation time including the effect of Bo inhomogeneity). As used herein, the term "relaxation time" refers to the above-described relaxation times either together or in the alternative. Other relevant relaxation times will be apparent to those of skill in the art. An exhaustive treatise on nuclear relaxation is available in Banci, L, et al. NUCLEAR AND ELECTRON RELAXATION, VCH, Weinheim, 1991, which is herein incorporated by reference.

As used herein, the term "diagnostically effective amount" refers to an amount of contrast agent that is sufficient to enable imaging of the contrast agent in cells, tissues, or organisms using imaging equipment.

DETAILED DESCRIPTION OF EMBODIMENTS

Magnetic resonance imaging (MRI) has become a popular technique for noninvasive imaging of opaque specimens due to its high spatial and temporal resolution. Exogenous agents manipulate relaxation times ($T_1$ and $T_2$) of water protons within a sample and enhance contrast in the image (see e.g., U.S. Pat. Nos. 7,354,568; 7,029,655; 6,770,261; 6,713,046; 6,713,045; 6,656,450; 5,980,862; 5,707,605; Pub. App. No. 20060088475; Pub. App. No. 20050002866; Pub. App. No. 20040170563; Pub. App. No. 20030198597; Pub. App. No. 20030135108; Pub. App. No. 20030053954; Pub. App. No. 20030021750; Pub. App. No. 20030004236; Pub. App. No. 20020197648; Pub. App. No. 20020098153; and Pub. App. No. 20020049308; herein incorporated by reference in their entireties). Principle limitations to current agents are amplification of signal, in vivo delivery, lack of multimodal validation, and the absence of biochemical reporters. The present invention provides, for example, improved signal enhancement and multimodal validation of MRI contrast agents by utilizing novel formulations of superparamagnetic nanoparticles and functionalizing them with multimodal moieties. Multimodal agents combine the advantages of several imaging techniques (e.g. MR and optical) allowing for coregistration and validation.

By developing novel nanomaterials that are platform-diagnostic, solutions to these fundamental barriers are provided. The present invention provides a novel class of enzyme-activated multimodal $T_1$-$T_2$ contrast agents for magnetic resonance imaging (MRI). $T_1$ and $T_2$ refer to the longitudinal and transverse relaxation times, respectively, of spins of the water protons surrounding the contrast agent. This type of contrast agent is classified as a multimodal agent because it allows for imaging and co-localization of data obtained in two MR modalities. The multimodal agents described herein comprise an entirely new class of multimodal MR contrast agents ($T_2+T_1$), which comprise a superparamagnetic $T_2$ nanoparticle functionalized with paramagnetic chelates. Further modification with an optical dye allows for imaging with a third modality. Such agents have great utility for the following reasons: 1) they provide significantly improved contrast in an image making better agents than are currently available, 2) they allow for validation in several imaging modalities ($T_1$, $T_2$ and an optional optical), 3) they exhibit unique magnetic properties and explore the physical interactions between two magnetic entities in relation to an MR contrast agent, 4) they possess many different properties which allow for optimization and significant versatility in applications of these agents, and 5) they can be designed to be activated in response to specific biological molecules or processes.

Two exemplary types of contrast agents are used in magnetic resonance imaging (MRI): 1) paramagnetic chelates, such as gadolinium diethylenetriaminepenta acetic acid (Gd-DPIA (Caravan et al. *Chem. Rev.* 1999, 99, 2293-2352, herein incorporated by reference in its entirety)) and 2) superparamagnetic (SPM) nanoparticles (Np). Superparamagnetic nanoparticles, namely magnetite, with diameters in the range of 10-100 nm have emerged over the past two decades as contrast agents for MRI. These nanoparticles are superparamagnetic and have a profound effect on the $T_2$ relaxation time of water protons when in a magnetic field. Compared to paramagnetic chelates, which are used for visualizing changes in $T_1$ relaxation times of protons, $T_2$ nanoparticles have greater sensitivity thus requiring a smaller amount of agent to achieve the desired contrast in an image.

Conventionally, coated superparamagnetic iron oxide (SPIO) and dextran-coated crosslinked iron oxide nanoparticles (CLIO) have been used as contrast agents and some forms are commercially available (Bulte et al. *Acad. Radiol.* 1998, 5 (suppl 1), S137-S140., herein incorporated by reference in its entirety). There are several examples in the literature of multimodal agents synthesized from CLIO particles (Werner et al. *J. Am. Chem. Soc.* 2007, 129, 1870-1871.; Liu et al. *Biochemical and Biophysical Research Communications* 2006, 347, 133-140.; Woods et al. *Chemical Society Reviews* 2006, 35, 500-511.; herein incorporated by reference in their entireties). However, these agents have several limitations, including 1) difficult synthetic reproducibility, 2) polydisperse particle sizes resulting from aqueous synthetic techniques that require extensive filtration and size selection, 3) limited ability to image biological events, and 4) relatively weak magnetism.

Recently, there have been several advances in non-hydrolytic high-temperature synthetic techniques, which lead to superparamagnetic nanoparticles with highly controlled size and shape, high monodispersity, and significantly improved magnetic properties (Song et al. *J. Am. Chem. Soc.* 2008, 130, 6662-6663., Frullano, L.; Meade, T. J. *JBIC* 2007, 12, 939-949., herein incorporated by reference in their entireties).

Additionally, there have been improvements in aqueous synthetic techniques that have demonstrated the control of size and shape, monodispersity, and high magnetism of non-hydrolytic techniques (Duimstra et al. *J. Am. Chem. Soc.* 2005, 127, 12847-12855.; herein incorporated by reference in its entirety). Because the need for multimodal agents is vast in applications such as cell migration, patterning, recognition, and fate mapping, the utilization of these newer synthetic techniques in developing multimodal contrast agents is contemplated. The present invention describes the design and synthesis of the first examples of $T_1$ and $T_2$ multimodal contrast agents, wherein the $T_1$ agent is covalently attached to the $T_2$ agent.

The multimodal agents described herein provide several improvements over existing technologies. Improvements include, but are not limited to, 1) an ability to image in two molecular resonance (MR) modalities and one optical modality (optional), 2) a change in magnetic properties is observed upon conjugation of a $T_1$ chelate to the $T_2$ nanoparticles including a drastic change in $T_2$ signal, 3) a new way to modulate $T_1$ relaxation times through conjugation and cleavage of the $T_1$-$T_2$ contrast agent, and 4) versatility of functionalization and conjugation strategies (e.g., non-cleavable vs. enzyme cleavable vs. enzyme-cleavable activatable), thereby allowing for detection and imaging of a variety of biological processes at the cellular level. The present invention describes embodiments for design and synthesis of an exemplary $T_1$-$T_2$ MRI contrast agent, which can be designed as a non-activated or activated agent.

In certain embodiments, the multimodal $T_1$-$T_2$ MRI contrast agent of the present invention further comprises an enzyme-cleavable peptide linker. In some embodiments, a paramagnetic Gd(III) chelate covalently attached to the surface of a superparamagnetic (SPM) nanoparticle (Np) through peptide linker that is cleaved in the presence of an enzyme. In some embodiments, the effects of the multimodal contrast agent on the T1 and T2 relaxation times, changes upon cleavage of the linker. In some embodiments, the paramagnetic Gd(III) chelate can be either diethylenetriaminepentaacetic acid (DTPA) or 1,4,7,10-tetraazacyclododecane-1,4,7,10-tetraacetic acid (DOTA) modified for attachment to a peptide linker. The peptide linker can be any peptide sequence containing the specific cleavage site for the enzyme of interest. Additionally, the peptide linker allows for specificity in imaging of biological systems. The nanoparticle can be any magnetic material exhibiting SPM behavior (typically observed in the size regime of 10-50 nm), for example, ferrite ($MFe_2O_4$, M=Fe, Co, Mn, Ni), iron, or cobalt. The nanoparticle, if used, can be coated by a surfactant to prevent aggregation. The surfactant coating should be biocompatible and have the ability to be further modified at the surface. Such biocompatible coatings include, but are not limited to, silica, PEG, and dextran. Finally, an optical dye can be attached to the $T_1$-$T_2$ agent for co-localization in a third imaging modality (optical) if so desired.

The basic concept of activation of the enzyme multimodal $T_1$-$T_2$ agent is illustrated in FIG. 1. The covalently-linked Gd(III) chelate ($T_1$) and SPM coated nanoparticle ($T_2$) have a certain relaxivity (defined as the slope of a plot of $1/T_{n-1,2}$ vs. concentration). In the presence of the enzyme specific for the sequence in the peptide linker, the $T_1$-$T_2$ agent is cleaved and with diffusion, is contemplated to express a change in relaxivity.

In an exemplary embodiment, the present invention provides for the design, synthesis, and characterization of an enzyme cleavable $T_1$-$T_2$ agent for the detection of MMP-7 enzyme activity. The $T_1$ agent is a Gd(III)-DTPA chelate and the $T_2$ agent is a SPM silica-coated cobalt ferrite core-shell particle with surface amine groups. The linker is a peptide backbone containing an MMP-7-specific cleavage site and a PEG spacer to provide extra room for the enzyme to interact with the peptide substrate as well as increase stability in aqueous conditions. More generally, this type of design provides applications for the diagnosis and monitoring of disease progression by real-time tracking of a variety of enzymes that are responsible for a multitude of diseases.

After enzymatic cleavage of the peptide, it is contemplated that the relaxation properties of the agent changes. In some embodiments, a PEG spacer was inserted between the peptide and the nanoparticle to allow ample space for the enzyme to interact with the peptide substrate. A $(PEG)_3$ spacer was chosen for initial studies due to cost and simplicity, however, many different lengths of this PEG spacer or other spacers are commercially available and equally amenable for use with these embodiments of the present invention. The exemplary amino acid sequence used is based on consensus sequences for MMP-7. Diethylenetriamine pentaacetic acid (DIPA) was chosen as the Gd(III) chelator due to cost and availability, however, other Gd(III) chelators may be used. Embodiments of the present invention include, but are not limited to, varying the peptide length and composition as well as by varying the length of the PEG spacer between the peptide and the nanoparticle. For example, in some embodiments, longer spacers are used. For example, in some embodiments, a Gd(III)-DTPA-modified MMP-7 peptide linker contains and longer spacer, $(PEG)_6$.

The following examples and embodiments are provided in order to demonstrate and further illustrate certain embodiments and aspects of the present invention and are not to be construed as limiting the scope thereof.

I. $T_1$ Contrast Agents

In some embodiments, the materials of the present invention comprise one or more $T_1$ contrast agents. In some embodiments, $T_1$ contrast agents cause a reduction in the $T_1$ relaxation time resulting in increased signal intensity on $T_1$ weighted images. In some embodiments $T_1$ contrast agents are known as positive contrast agents. In some embodiments, $T_1$ contrast agents are small molecular weight compounds. In some embodiments, $T_1$ contrast agents contain a paramagnetic metal ion as the active element of the paramagnetic contrast agents. Exemplary paramagnetic contrast agents suitable for use in the present compositions include, for example, stable free radicals, such as, for example, stable nitroxides, as well as compounds comprising transition, lanthanide and actinide elements, which may, if desired, be in the form of a salt or may be covalently or non-covalently bound to complexing agents, including lipophilic derivatives thereof, or to polypeptide-containing macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). The foregoing elements may, if desired, be in the form of a salt, including inorganic and organic salts.

These elements may also, if desired, be complexed, for example, through covalent or noncovalent association, to one or more complexing agents, including lipophilic derivatives thereof, or to polypeptide-containing macromolecules. Preferable complexing agents for the present invention include, for example, diethylenetriaminepentaacetic acid (DTPA), ethylene-diaminetetraacetic acid (EDTA), 1,4,7,10-tetraazacyclododecane-N,N',N'',N'''-tetraacetic acid (DOTA), 1,4,7,10-tetraazacyclododecane-N,N',N''-triacetic acid (DOTA), 3,6,9-triaza-12-oxa-3,6,9-tricarboxymethylene-10-carboxy-13-phenyl-trideca noic acid (B-19036), hydroxybenzylethylenediamine diacetic acid (HBED), N,N'-bis(pyridoxy)-5-phosphate)ethylene diamine, N,N'-diacetate (DPDP), 1,4,7-triazacyclononane-N,N',N"-triacetic acid (NOTA), 1,4,8,11-tetraazacyclotetradecane-N,N',N",N"'-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)-ethylenediamine-N,N'-diacetate (EDTA-DDP); N,N'-bis-(carboxy-octadecylamido-methyl-N-2,3-dihydroxypropyl)-ethylenediamine-N,N'-diacetate (EDTA-ODP); N,N'-Bis (carboxy-laurylamidomethyl-N-2,3-dihydroxypropyl) ethylenediamine-N,N'-diacetate (EDTA-LDP); and the like, including those described in U.S. Pat. No. 5,312,617, the disclosures of which are hereby incorporated herein by reference, in their entirety. Preferable polypeptide-containing macromolecules include, for example, albumin, collagen, polyarginine, polylysine, polyhistidine, gamma-globulin and beta-globulin, or any polypeptide sequence.

Suitable complexes therefore include, but are not limited to: Mn(I)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(II)-EDTA, Cu(I)-EDTA, or iron-desferrioxamine, especially Mn(II)-DTPA or Gd(III)-DTPA.

Additionally, the present invention may utilize a number of different magnetic resonance contrast agents that are well known in the art, and are disclosed in, for example, U.S. Pat. Nos. 5,141,740; 5,078,986; 5,055,288; 5,010,191; 4,826,673; 4,822,594; and 4,770,183, which are incorporated herein by reference. Such magnetic resonance contrast agents include many different paramagnetic contrast agents, for example, gadolinium compounds.

II. $T_2$ Contrast Agents

In some embodiments, the materials of the present invention comprise one or more $T_2$ contrast agents. In some embodiments, $T_2$ contrast agents cause a reduction in the $T_2$ relaxation time resulting in increased signal intensity on $T_2$ weighted images. In some embodiments, $T_2$ contrast agents cause a reduction in both $T_1$ and $T_2$ relaxation. In some embodiments, the $T_2$ contrast agent comprises a nanoparticle. In some embodiments, the nanoparticle comprises a material that exhibits superparamagnetic (SPM) behavior. In some embodiments, the present invention provides a nanoparticle with a diameter of approximately 5-50 nm (e.g. 5 nm . . . 10 nm . . . 20 nm . . . 30 nm . . . 40 nm . . . 50 nm) In some embodiments, the present invention provides a nanoparticle with a diameter of greater than 50 nm. In some embodiments, the nanoparticle of the present invention comprises core comprised of for example ferrite ($MFe_2O_4$, M=Fe, Co, Mn, Ni), iron, cobalt, or other. In some embodiments the nanoparticle is coated with a biocompatible surfactant that permits further modification, prevents aggregation, and/or renders the nanoparticle useful in a biological setting, although the present invention is not limited to any particular mechanism of action and an understanding of the mechanism of action is not necessary to practice the present invention. Such biocompatible coatings include, but are not limited to, silica, PEG, and dextran. In some embodiments, the surface of the nanoparticle is functionalized to allow further modification, although the present invention is not limited to any particular mechanism of action and an understanding of the mechanism of action is not necessary to practice the present invention. In some embodiments the surface modification of the nanoparticles includes thiol-modification.

III. Linker Region

In some embodiments of the present invention, the $T_1$ and $T_2$ contrast agent portions are linked, either directly or linked via a suitable linker. The present invention is not limited to any particular linker group. Indeed, a variety of linker groups are contemplated, suitable linkers could comprise, but are not limited to, alkyl groups, ether, polyether, alkyl amide linker, a peptide linker, a modified peptide linker, a Poly(ethylene glycol) (PEG) linker, a streptavidin-biotin or avidin-biotin linker, polyaminoacids (eg. polylysine), functionalised PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (WO94/08629, WO94/09056 and WO96/26754, herein incorporated by reference in their entireties), oligonucleotide linker, phospholipid derivatives, alkenyl chains, alkynyl chains, disulfide, or a combination thereof.

In some embodiments the linker comprises a single chain connecting one $T_1$ contrast agent portion to one $T_2$ contrast agent portion. In some embodiments, there are multiple linkers connecting multiple $T_1$ contrast agent portions to a single $T_2$ contrast agent portion. In some embodiments, a linker may connect multiple $T_1$ contrast agent portions to each other. In some embodiments, a linker may connect multiple $T_2$ contrast agent portions to each other. In some embodiments, a linker attaches an additional functional portion to a $T_1$ and/or $T_2$ contrast agent. In some embodiments, a linker may be branched, connecting more than two $T_1$ and/or $T_2$ contrast agent portions. In some embodiments, the linker may be flexible, or rigid.

In some embodiments, the linker of the present invention is cleavable or selectively cleavable. In some embodiments, the linker is cleavable under at least one set of conditions, while not being substantially cleaved (e.g. approximately 50%, 60%, 70%, 80%, 90%, 95%, 99%, or greater remains uncleaved) under another set (or other sets) of conditions. In some embodiments, the linker is susceptible to cleavage under specific conditions relating to pH, temperature, oxidation, reduction, UV exposure, exposure to radical oxygen species, chemical exposure, light exposure (e.g. photo-cleavable), etc.

In some embodiments, the linker region is photocleavable. That is, upon exposure to a certain wavelength of light, the linker region is cleaved, allowing release of the connected contrast agents. This embodiment has particular use in developmental biology fields (cell lineage, neuronal development, etc.), where the ability to follow the fates of particular cells is desirable. A particularly preferred class of photocleavable linkers are the O-nitrobenzylic compounds, which can be synthetically incorporated via an ether, thioether, ester (including phosphate esters), amine or similar linkage to a heteroatom (particularly oxygen, nitrogen or sulfur). Also of use are benzoin-based photocleavable linkers. A wide variety of suitable photocleavable moieties is outlined in the Molecular Probes Catalog, supra.

In some embodiments, the linker is susceptible to enzymatic cleavage (e.g. proteolysis). In some embodiments of the present invention, the $T_1$ and $T_2$ contrast agent portions are linked, via a cleavable linker. The present invention is not limited to any particular linker group. In some embodiments, the cleavable linker region contains a peptide portion. In some embodiments, the peptide portion of the cleavable linker region is cleavable. In some embodiments, the peptide portion of the cleavable linker region is enzymatically cleavable. In some embodiments, the peptide portion of the cleavable linker region is configured to be cleaved by proteolysis. In some embodiments the cleavable linker contains a specific proteolytic site.

In some embodiments, in addition to the peptide portion of the cleavable linker region, an additional linker portion is contemplated. Indeed, a variety of additional linker groups are contemplated, suitable linkers could comprise, but are not limited to, alkyl groups, ether, polyether, alkyl amide linker, a peptide linker, a modified peptide linker, a Poly(ethylene glycol) (PEG) linker, a streptavidin-biotin or avidin-biotin linker, polyaminoacids (eg. polylysine), functionalised PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (WO94/08629, WO94/09056 and WO96/26754, herein incorporated by reference in their entireties), oligonucleotide linker, phospholipid derivatives, alkenyl chains, alkynyl chains, disulfide, or a combination thereof.

In some embodiments the cleavable linker is a substrate for an enzyme; many enzyme substrate pairs can be contemplated. In some embodiments, the cleavable linker is a substrate for cathepsin B, cathepsin D, cathepsin K, β-glucuronidase, heparanase, hepsin, matrix metalloproteinase (MMP), or other enzymes. In some embodiments, the peptide portion of the cleavable linker is a MMP-7 peptide linker, or a portion or similar sequence thereof. In some embodiments, the peptide portion of the cleavable linker is cleavable by the MMP-7 enzyme. In some embodiments, the peptide portion of the cleavable linker is of the sequence Ala-Pro-Leu-Ala-Leu-Trp-Ala, Ala-Pro-Leu-Ala, a similar sequence, or a portion thereof. In some embodiments, the cleavable linker comprises a MMP-7 peptide and a spacer (e.g. $(PEG)_6$, $(PEG)_3$, etc.).

Suitable peptide substrates for MMPs include the peptide sequence Pro-Met-Ala-Leu-Trp-Met-Arg (Netzel-Arnett, S., et al., 1993, Biochem., 32: 6427-6432, herein incorporated by reference in its entirety). Recognition of the peptide sequence by an MMP can result in cleavage of the peptide sequence Pro-Met-Ala-Leu-Trp-Met-Arg to yield two peptide fragments: -Pro-Met-Ala- and -Leu-Trp-Met-Arg. Preferred peptide substrates include -Ala-Leu-.

In some embodiments, the linker sequence can be designed to be peptide substrates for MMPs having, for example, the formula:

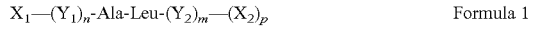

$X_1$—$(Y_1)_n$-Ala-Leu-$(Y_2)_m$—$(X_2)_p$    Formula 1

Taken together Formula 1 comprises a linker that can bind to an MMP, minimally including an MMP substrate (cleavage site).

"$X_1$" and "$X_2$" refer to linkers; suitable linkers are defined above. Generally suitable linkers include, but are not limited to, alkyl and aryl groups, including substituted alkyl and aryl groups and heteroalkyl (particularly oxo groups) and heteroaryl groups, including alkyl amine groups, as defined above. Some preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Other preferred linkers include p-aminobenzyl, methyl, ethyl, propyl, butyl, pentyl, hexyl, acetic acid, propionic acid, aminobutyl, p-alkyl phenols, 4-alkylimidazole, carbonyls, O⁻, COO⁻, —(CH₂CO)—, glycols, etc. In addition, the linkers can be or include a carbohydrate group, a lipid group, a nucleic acid group, a phosphorus moiety, all or a portion of a ligand for a cell surface receptor, and an antibody. For example, to increase the solubility of the MRI agent, $X_1$ can comprise an alkyl group attached to a carbohydrate moiety and $X_2$ can comprise a carbohydrate moiety. "p" is an integer from 0 to 1. When "p" equals 0, $X_2$ is absent; when p=1, $X_2$ is present. "$Y_1$" and "$Y_2$" refer to amino acids. The amino acids can be naturally occurring amino acids, although amino acid analogs and peptidomimitic structures are also useful in the compositions and methods of the present invention. "n" and "m" are integers, that are each independently of the other, an integer from 0 to 10. In preferred embodiments, n and m are each independently of the other, an integer from 0 to 5. Amino acids for "$Y_1$" and "$Y_2$" are chosen independently of each other. Thus, "$Y_1$" and "$Y_2$" can comprise the same amino acids, different amino acids, or comprise one or more amino acids in common. For example, both "$Y_1$" and "$Y_2$" can comprise the amino acid -Met-. In other embodiments, "$Y_1$" can comprise the amino acids -Pro-Met- and "$Y_2$" can comprise the amino acids -Trp-Met-Arg-, and so forth. In yet other embodiments, "$Y_1$" and/or "$Y_1$" can be absent.

In one embodiment, the peptide may have multiple -Ala-Leu-sequences such that interaction with the MMP causes a "chewing off of the peptide." In addition, these peptides can have higher affinity for the enzyme.

In some embodiments, the linker region comprises the composition according to structural Formula 1. In these embodiments, "$X_1$" and "$X_2$" are linkers as defined above, and "$Y_1$" and "$Y_2$" comprise at least one amino acid that may be the same amino acid or a different amino acid.

In one specific embodiment, $X_1$ is —(CH₂CO)—, n equals 2 and $Y_1$ is -Pro-Met-, m equals 3 and $Y_2$ is -Trp-Met-Arg, and p equals 0.

In another specific embodiment, $X_1$ is —(CH₂CO)—, n equals 1 and $Y_1$ is -Met-, m equals 3 and $Y_2$ is -Trp-Met-Arg, and p equals 0.

In yet another specific embodiment of the present invention, $X_1$ is —(CH₂CO)—, n equals 0, m equals 3 and $Y_2$ is -Trp-Met-Arg, and p equals 0.

In other embodiments, the MMP peptide portion of Formula 1 can be replaced with a small molecule or other moiety that can bind to an MMP, or which is capable of binding to, or being cleaved by another enzyme.

There are a number of other MMP substrates that can be used. The substrates are particularly useful as cancer cleavage sites with the use of coordination site barriers. These MMP substrates include, but are not limited to, 1,10-phenanthroline; CT1847; AG3319, AG3340 (also called Prinomastat), AG3287, AG3293, AG3294, AG3296; 2-mercaptoacetyl L-phenyl-alanyl-L-leucine; HSCH₂CH[CH₂CH(CH₃)₂]CO-Phe-Ala-NH₂; OPB-3206; Furin Inhibitor; 3,4-dihydro-1-oxo-1,2,3,-benzotriazine-3-(3-tetrahydrofuranyl)-carbonate (IW-1); 1,2-dihydro-3,6-dioxo-2-phenyl-pyridazine-1-methylcarbonate (LW-2); 3,4-dihydro-1-oxo-1,2,3,-benzotriazine-3-(2-methoxy)ethylcarbonate (LW-3); 1,2-dihydro-2-ethoxycarbonyl-(1-oxo-isochinolin-5-yl) ethylcarbonate (LW-4); 1(2H)-phtalazinone-2-(4-methoxyphenyl) carbonate (LW-5); N-[2(R)-2-(hydroxamido carbonylmethyl)-4-methyl pentanoyl]-L-tryptophane methylamide also called GM6001, Galardin and ilomastat; BAY 12-9566; Neovastat (AE-941); BB-1101; G1129471; Ph(CH₂NH-D-$R_{rev}$CO—CH₂CH₂D)₂ also called FC-336; Mca-Pro-Leu-Gly-Leu-Dpa-Ala-Arg-NH₂ (cleavage occurs between Gly and Leu); DNP-Pro-Leu-Gly-Ile-Ala-Gly-Arg-OOOH (cleavage occurs between Gly and Leu); carboxymethyl transferrin (Cm-Tf); (7-methoxycoumarin-4-yl)acety-1-PLGP-[3-(2,4-dinitrophenyl)-L-2,3 diaminopropionyl]-AR-NH₂; (7-methoxycoumarin-4-yl)acetyl-PLAQAV-[3-(2,4-dinitrophenyl)-L-2,3 diaminopropionyl]-RSSSR—NH₂; Ac-PLG-[2-mercapto-4-methylpentanoyl]-L-G-OEt; Peptide I:

GPLGLRSW; and Peptide II: GPLPLRSW. See generally, Greenwald et al. Bone 22, 33-38 (1998); Kolb et al., J. Neuroimmunol. 84, 143-150 (1998); Charoenrat et al. Int. J. Cancer 86, 307-317 (2000); Uzui et al. Atherosclerosis 149, 51-59 (2000); Montesano et al. Cell Growth Differ. 10, 317-332 (1999); Yip et al. Invest New Drugs 17, 387-399 (1999); Price et al. Clin. Cancer Res. 5, 845-854 (1999); Santos et al. Clin. Exp. Metastasis 15, 499-508 (1997); Barletta et al. Invest Opthalmol. Vis. Sci. 37, 20-28 (1996); Maquoi et al. FEBS Lett. 424, 262-266 (1998); Makela et al. Exp. Cell Res. 251, 67-78 (1999); Hao et al. Exp. Eye Res. 69, 595-601 (1999); Hao et al. Exp. Eye Res. 68, 565-572 (1999); Wallace et al. Clin. Exp. Immunol. 118, 364-370 (1999); Maquoi et al. J. Biol. Chem. 275, 11368-11378 (2000); Ikeda et al. Anticancer Res. 18, 4259-4265 (1998); Schultz et al. Invest Opthalmol. Vis. Sci. 33, 3325-3331 (1992); Buchardt et al. Chem. Eur. J. 5, 2877-2884 (2000); Dahlberg et al. Arthritis Rheum. 43, 673-682 (2000); Lombard et al. Cancer Res. 58, 4001-4007 (1998); Lein et al. Prostate 43, 77-82 (2000); Brown et al. Med. Oncol. 14, 1-10 (1997); Garbett et al. Mol. Pathol. 52, 140-145 (1999); Itoh et al. J. Biochem. (Tokyo) 119, 667673 (1996); Wang et al. J. Biol. Chem. 274, 3304333049 (1999); Ohkubo et al. Biochem. Biophys. Res. Commun. 266, 308-313 (1999), all of which are expressly incorporated by reference.

In some embodiments, the linker region may contain additional functionalities. In some embodiments, the linker region is a substrate or inhibitor for matrilysin (also sometimes referred to in the literature as pump-1 and MMP-7). It has been implicated in gastric, colon, breast and prostate cancers, and is clearly implicated in metastasis and potentially growth and invasion as well. It is a zinc metalloenzyme, with a thermolysin-type Zn binding region, and is activated by cystein switch. It is exclusively associated with tumor cells, unlike other MMPs, and its mRNA expression is induced by IL-β It is secreted from epithelial cells of glandular tissue. Its substrates include, but are not limited to, proteglycans, laminin, fibronectin, gelatins, collagen IV, elastin, entactin and tenascin. Its inhibitors include a variety of metal chelators and tissue inhibitors (TIMPs). See MacDougall et al., Cancer and Metastasis Rev. 14:351 (1995); Stetler-Stevenson et al., FASEB 7:1434 (1993); Mirelle Gaire et al., J. Biol. Chem. 269:2032 (1994), all of which are expressly incorporated by reference.

In some embodiments, the linker region is a substrate or inhibitor for the extracellular statum corneum chymotryptic enzyme (SCCE), which has been implicated in ovarian cancer. This enzyme is involved in tumor invasion and metastasis by allowing implantation and invasion of neighboring cells. It is a serine protease with a standard catalytic triad (ser-his-asp) in its active site, and it may activate MMPs. Its substrates include gelatin and collagen, and is inhibited by the D43 mAb. See Tantimoto et al., supra; Hansson et al., J. Biol. Com. 269:19420 (1994), both of which are incorporated by reference.

In some embodiments, the linker region is a substrate or inhibitor for seprase. Seprase has been implicated in breast cancer and is involved in an early event in the progression from a non-invasive premalignant phenotype to the invasive malignant phenotype. It is a 170 kDa dimer, and is a serine integral membrane protease (with a putative standard catalytic triad) with gelanitinase activity. The monomer 97 kDa form is inactive. The catalytic domain is exposed to the extracellular environment. Seprase is overexpressed in neoplasic invasive ductal carcinoma (IDC) cells and exhibits low levels of expression in benign proliferative tissue or normal breast cells. It also may activate MMPs. It degrades gelatin and collagen. See Kelly et al, Mod. Path. 11 (9):855 (1998), incorporated by reference.

In some embodiments, the linker region is a substrate or inhibitor for Type IV collegenase (also sometimes referred to as MMP-2 and gelantinase A). This enzyme has been implicated in breast, colon and gastic cancers, and is involved in the penetration of membrane material and the invasion of stroma. It is a 72 kDa neutral Zn metalloendoproteinase that degrades basement membrane type IV collagen and gelatin in a pepsin-resistant domain. It is activated by a cysteine switch and is a membrane type I MMP. It is secreted extracellularly by epithelial cells, fibroblasts, endothelial cells and macrophages as an inactivated form. Its substrates include, but are not limited to, type IV collagen, gelatins, fibroblasts, type V coliagens, type VII coliagen, proMMP-9 and elastins. Its inhibitors include TIMP-2. See Poulsom et al., Am. J. Path. 141:389 (1992); Stearns et al., Cancer Res. 53:878 (1993); Nakahara et al., PNAS USA 94:7959 (1997); and Johnson et al., Curr. Opin. Chem. Biol. 2:466 (1999), all of which are expressly incorporated by reference.

In some embodiments, the linker region is a substrate or inhibitor of HER-2/neu protein (sometimes referred to as erb-B-2). HER-2/neu is a 185 kDa transmembrane phosphoglycoprotein with tyrosine kinase activity that has been implicated in breast, ovarian and non-small cell (NSC) lung carcinoma. High serum levels have been shown to correlate with poor prognosis and increased resistance to endocrine therapy, and it has been identified in 25-30% of all breast cancers. Its ligands are NDF/heregulins and gp 30 (which is related to TGFα. See Codony-Serat et al., Cancer Res. 59:1196 (1999); Earp et al., Breast Canc. Res. Treat. 35:115 (1995); Depowski et al., Am. J. Clin. Pathol. 112:459 (1999), all of which are expressly incorporated by reference.

In some embodiments, the linker region binds and/or inhibits ras, which has been implicated in NSC lung cancer. Ras is an essential signal transduction protein though to follow overexpression of HER2/neu protein, and is also related to p53 overexpression. Deregulated expression of ras results in uncontrolled cell growth and cancer, with overexpression being correlated with drug resistance. It functions as a surface antigen that is recognized by antibodies and T-cells. See Shackney et al., J. Thorac. Cadio. Surg 118:259 (1999), incorporated by reference.

In some embodiments, the linker region binds to RCAS 1. RCAS 1 has been implicated in uterine, ovarian, esophageal and small cell lung carcinomas, gastic colon, lung and pancreatic cancers. It is a type II membrane protein and acts as a ligand for a receptor on normal peripheral lymphocytes (e.g. T and NK cells) followed by inhibition of the receptor cell and cell death. It neutralizes immunoprotection by lymphocytes. It is expressed on cancer cell surfaces and in the extracellular medium, but is not detected in normal cells. See Nakashima et al., Nature Med. 5:938 (1999) and Villunger et al., Nature Medicine 5:874 (1999), all of which are incorporated by reference.

In some embodiments, the linker region binds to reg protein (including reg Iα and regIβ and pap). Reg has been implicated in pancreatic cancer, colorectal and liver carcinomas, and is present in acinar cell carcinoma, pancreatoblastoma, solid and cystic tumors and ductal cell carcinoma. See Rechreche et al., Int. J. Cancer 81:688 (1999) and Kimura et al., Cancer 70:1857 (1992), all of which are incorporated by reference.

In some embodiments, the linker region binds to thrombospondin-1, which has been implicated in pancreatic adenocarcinoma. It activates TGF-β, which is a key fibrogenic factor resulting in desmoplasia. See Cramer et al, Gastrent. 166 (4 pt 2):pA1116 (G4840) (1999); incorporated by reference.

In some embodiments, the linker region is a substrate or inhibitor for a caspase enzyme, including caspase-1 (also sometimes referred to as IL-1β), -3, -8, -9, etc. Caspases are also cysteine proteases which are putatively involved in the apoptosis cascade. Many of the caspases are generally made as proenzymes of 30-50 kDa. They cleave after asp residues with recognition of 4 amino acids on the N-side of the cleavage site.

In some embodiments, the linker region binds to alpha 1-acid glycoprotein (AAG). AAG has been suggested as a prognostic aid for glioma and metastatic breast and other carcinomas. AAG is highly soluble and is a single 183 amino acid polypeptide chain. It is characterized by a high carbohydrate (45%) and sialic acid (12%) content, and a low isoelectric point (pH 2.7). It has been implicated in binding of many drugs, including propranolol, imipramine and chloropromazine, all of which can be used as a guarding moiety.

In some embodiments, the linker region is involved in angiogenesis. There are a wide variety of moieties known to be involved in angiogenesis, including, but not limited to, vascular endothelial growth factors (VEGF; including VEGF-A, VEGF-B, VEGF-C and VEGF-D), FGF-1 (aFGF), FGF-2 (bFG F), FGF-3, FGF-4, hepatocyte growth factor (HG F, scatter factor), thymidine phosphorylase, angiogenin, IL-8, TNF-α, leptin, transforming growth factors (TGF-α, TGF-β), platelet-derived growth factor, proliferin, and granulocyte colony stimulating factor (G-CSF). Known angiogenesis inhibitors include, but are not limited to, platelet factor 4, thrombospondin-1, interferons (IFN-α, IFN-β, IFN-γ), IL-1, IL-2, vascular endothelial growth inhibitor (VEGI), 2-methoxyestradiol, tissue inhibitors of MMPs (TIMPs), proliferin related protein, angiostatin, endostatin, amion terminal fragment of u-PA (ATF), thalidomide, TNP-470/AGM-1470, carboxyamidotriazole, maspin, AG3340, marimastat, BAY9566, CSG-27023A, gly-arg-gly-asp-ser (GRGDS), tyr-Ile-gly-ser-arg (YIGSR) and ser-Ile-lys-val-ala-val (SIKVAV). See van Hinsbergh et al, Annals of Oncology 10 Supp. 4:60 (1999) and references therein; Li et al., Human Gene Therapy 10(18):3045 (1999); Duenas et al., Investigative Opthalmology, 1999; Bauer et al., J. Pharmacology & Experimental Therapeutics 292(1):31 (2000); Zhang et al., Nature Medicine 6(2):196 (2000); Sipose et al., Annal of the New York Academy of Sciences 732:263 (1994 and references therein); Niresia et al, Am. J. Pathology 138(4):829 (1991); Yamamura et al., Seminars in Cancer Biology 4(4):259 (1993), all of which are incorporated by reference.

As will be appreciated by those skilled in the art, the potential list of suitable cancer enzyme targets is quite large. Once the target cancer enzyme is identified or chosen, enzyme substrate linker can be designed using well known parameters of enzyme substrate specificities as is generally known in the art.

In some embodiments, the present invention may contain a non-cleavable linker or linkers, in addition to the cleavable linker or linkers. Suitable non-cleavable linkers could comprise any of the linker types above, and could perform any of the connective functions above.

IV. Additional Functional Portions

In some embodiments, the present invention may contain one or more additional functional portions, in addition to the $T_1$ and $T_2$ contrast agent portions and the linker region. In some embodiments, the present invention allows co-localization of $T_1$ and $T_2$ contrast agents with an additional functional portion. In some embodiments, an additional functional portion is attached to the $T_1$ and/or $T_2$ contrast agent portions by any of the linkers listed above. In some embodiments, an additional functional portion is attached to the $T_2$ contrast agent portions by any of the linkers listed above.

In some embodiments, an additional functional portion is an optical dye. In some embodiments, the additional functional portion is a chromophore. In some embodiments, an optical dye functional portion allows co-localization of optical imaging with MRI. In some embodiments, the present invention allows co-localization of $T_1$ and $T_2$ contrast agents with an optical dye functional portion. In some embodiments, the optical dye is selected from the group including, but not limited to acridine dyes, anthraquinone dyes, arylmethan dyes, azo dyes, cyanine dyes, diazonium dyes, nitro dyes, nitroso dyes, phenaanthridine dyes, pthalocyanine dyes, quinine-imine dyes, indamins, indophenols dyes, oxazin dyes, oxazone dyes, thiazin dyes, thiazole dyes, xanthenes dyes, fluorene dyes, pyronin dyes, fluorine dyes, rhodamine dyes, etc. In some embodiments, the optical dye is a fluorophore selected from the list including, but not limited to (E)-stilbene, (Z)-Stilbene, 7-Amino-actinomycin D, Acridine orange, Acridine yellow, Alexa Fluor, Auramine 0, Auramine-rhodamine stain, Benzanthrone, 9,10-Bis(phenylethynyl)anthracene, 5,12-Bis(phenylethynyl)naphthacene, CFDA-SE, CFSE, Calcein, Carboxyfluorescein, 1-Chloro-9, 10-bis(phenylethynyl)anthracene, 2-Chloro-9,10-bis(phenylethynyl)anthracene, Coumarin, Cyanine, DAPI, Dark quencher, DiOC6, DyLight Fluor, Ethidium bromide, Fluorescein, Fura-2, Fura-2-acetoxymethyl ester, Green fluorescent protein (GFP) and modifications of GFP that have different absorption/emission properties, HiLyte Fluor, Hoechst stain, Indian yellow, Indo-1, Luciferin, Nile red, Perylene, Phycobilin, Phycoerythrin, Phycoerythrobilin, Propidium iodide, Pyranine, Rhodamine, RiboGreen, Rubrene, Ruthenium(II) tris(bathophenanthroline disulfonate), SYBR Green, Sulforhodamine 101, Sulforhodamine B, TSQ, Texas Red, Umbelliferone, and Yellow fluorescent protein.

In some embodiments, an additional functional portion is a biomolecule, such as for example, a ligand, antibody, peptide, polypeptide, protein, nucleic acid, polysaccharide, carbohydrate, lipid, glycoprotein, phospholipid, sterol, hormone, disaccharide, amino acid, nucleotide, phosphate, monsacharide, etc. In some embodiments, a biomolecule functional portion serves to localize the present invention in a specific cell type, for example, blastomere, embryonic stem cell, erythrocyte, fibroblast, hepatocyte, myoblast, myotube, neuron, oocyte, osteoblast, osteoclast, T-Cell, zygote, prokaryotic cell, a specific bacteria, plant cells, fungal cells, etc. In some embodiments, a biomolecule functional portion serves to localize the present invention in a specific cellular region, for example cytoplasm, nucleus, intracellular space, golgi complex, endoplasmic reticulum, mitochondria, chloroplasts, etc. In some embodiments, a biomolecule functional portion serves to localize the present invention in a specific tissue, for example, epithelial, connective, muscle, neural, etc. In some embodiments, a biomolecule functional portion serves to localize the present invention in specific diseased cells, for example, cancer cells, virally infected cells, etc. In some embodiments, a biomolecule functional portion serves to interact with native biomolecules in a subject, sample, tissue, or cell, such as for example, cell surface markers, antibodies, receptor proteins, nucleic acid, specific classes of proteins, etc.

In some embodiments, an additional functional portion is a biomolecule which serves as a targeting moiety. By "targeting moiety" herein is meant a functional group which serves to target or direct the complex to a particular location, cell type, diseased tissue, or association. In general, the targeting moiety is directed against a target molecule. As will be appreciated by those in the art, the MRI contrast agents of the invention may be injected intravenously; thus targeting moieties may be those that allow concentration of the agents in a particular localization. In some embodiments, the agent is partitioned to the location in a non-1:1 ration. Thus, for example, antibodies, cell surface receptor ligands and hormones, lipids, sugars and dextrans, alcohols, bile acids, fatty acids, amino acids, peptides and nucleic acids may all be attached to localize or target the contrast agent to a particular site.

In some embodiments, the targeting moiety allows targeting of the MRI agents of the invention to a particular tissue or the surface of a cell. In some embodiment the MRI agents of the invention need not be taken up into the cytoplasm of a cell to be activated.

In some embodiments, the targeting moiety is a peptide. For example, chemotactic peptides have been used to image tissue injury and inflammation, particularly by bacterial infection; see WO 97/14443, hereby expressly incorporated by reference in its entirety.

In some embodiments, the targeting moiety is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In some embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992), herein incorporated by reference in their entirety).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988), herein incorporated by reference in their entireties), by substituting rodent CDRs or CDR sequences for the corresponding sequences of a human antibody. Accordingly, such "humanized" antibodies are chimeric antibodies (U.S. Pat. No. 4,816,567, herein incorporated by reference), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol. 227:381 (1991); Marks et al., J. Mol. Biol. 222:581 (1991), herein incorporated by reference in their entireties). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1):86-95 (1991), incorporated by reference). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology, 14:826 (1996); Lonberg and Huszar, Intern. Rev. Immunol. 13:65-93 (1995), all of which are incorporated by reference in their entireties.

Bispecific antibodies are monoclonal, preferably human or humanized, antibodies that have binding specificities for at least two different antigens. In the present case, one of the binding specificities is for a first target molecule and the other one is for a second target molecule. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature 305:537-539 (1983), incorporated by reference). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J. 10:3655-3659 (1991), incorporated by reference.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology 121:210 (1986), incorporated by reference.

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980, incorporated by reference), and for treatment of HIV infection (WO 91/00360; WO 92/200373; EP 03089, incorporated by reference). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980, incorporated by reference.

In some embodiments, the antibody is directed against a cell-surface marker on a cancer cell; that is, the target molecule is a cell surface molecule. As is known in the art, there are a wide variety of antibodies known to be differentially expressed on tumor cells, including, but not limited to, HER2.

In some embodiments, antibodies against physiologically relevant carbohydrates may be used, including, but not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimulating hormone, norepinephrine, parathyroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In some embodiments, the targeting moiety is a carbohydrate. By "carbohydrate" herein is meant a compound with the general formula $Cx(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, man nose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, etc.) have been used to deliver MRI agents into cells; see U.S. Pat. No. 5,554,386, hereby incorporated by reference in its entirety. In some embodiments, the use of carbohydrate targeting moieties can allow differential uptake into different tissues or altered half-life of the compound.

In some embodiments, the targeting moiety is a lipid. "Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moiety may be used to either allow the internalization of the MRI agent to the cell cytoplasm or localize it to a particular cellular compartment, such as the nucleus.

In some embodiments, the targeting moiety is all or a portion of the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); Baldin et al., EMBO J. 9:1511 (1990); Watson et al., Biochem. Pharmcol. 58:1521 (1999), all of which are incorporated by reference.

In some embodiments, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499-509; the human retinoic acid receptors nuclear localization signal (ARRRRP); NF-κB p50 (EEVQRKRQKL; Ghosh et al., Cell 62:1019 (1990); NF-κB p65 (EEKRKRTYE; Nolan et al., Cell 64:961 (1991); and others (see for example Boulikas, J. Cell. Biochem. 55(1):32-58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449-458, 1982 and Dingwall, et al., J. Cell Biol., 107:641-849; 1988, all of which are incorporated by reference). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367-390, 1986; Bonnerot, et al., Proc. Natl. Acad. Sci. USA, 84:6795-6799, 1987; Galileo, et al., Proc. Natl. Acad. Sci. USA, 87:458-462, 1990, all of which are incorporated by reference.

In a preferred embodiment, targeting moieties for the hepatobiliary system are used; see U.S. Pat. Nos. 5,573,752 and 5,582,814, both of which are hereby incorporated by reference in their entirety.

In some embodiments, an additional functional portion is a tag allowing the present invention to be used with additional imaging modalities. In some embodiments, an additional imaging modality will provide co-localization of multiple imaging modalities. In some embodiments, an additional imaging modality will provide co-localization of an additional imaging modality with $T_1$ and $T_2$ contrast agents for MRI. In some embodiments, an additional functional portion allows the present invention to be used with, for example, nuclear medicine, molecular imaging, positron emission tomography (PET), single photon emission computed tomography (SPECT), optical imaging, infrared imaging, fluoroscopy, angiography, computed tomography (CT) scanning, etc.

VI. Administration

The present invention provides contrast agents to be used in the generating an image of a human or non-human subject involving administering the contrast agent to the subject (e.g. vascularly, via the gastrointestinal tract, etc.) and generating an image of at least a part of the subject to which the contrast agent has distributed.

In some embodiments, the present invention is used by administering a multi-modal contrast agent of the present invention to a subject. Known methods for administering therapeutics and diagnostics can be used to administer contrast agents for practicing the present invention. For example, fluids that include pharmaceutically and physiologically acceptable fluids, including water, physiological saline, balanced salt solutions, buffers, aqueous dextrose, glycerol or the like as a vehicle, can be administered by any method used by those skilled in the art. These solutions are typically sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected. The invention further provides formulations comprising the contrast agent of the invention and a pharmaceutically acceptable excipient, wherein the contrast agent is formed according to any of the above described embodiments, and wherein the formulation is suitable for administration as an imaging enhancing agent and the contrast agent is present in an amount sufficient to enhance a magnetic resonance tomography image. These agents can be administered by any means in any appropriate formulation. Detergents can also be used to stabilize the composition or the increase or decrease the absorption of the composition. Other physiologically acceptable compounds include wetting agents, emulsifying agents, dispersing agents or preservatives that are particularly useful for preventing the growth or action of microorganisms. One skilled in the art would appreciate that the choice of a acceptable carrier, including a physiologically acceptable compound depends, e.g. on the route of administration and on the particular physio-chemical characteristics of any co-administered agent.

Methods of introduction include, but are not limited to, intradermal, intramuscular, intraperitoneal, intravenous, subcutaneous, intranasal, rectal, vaginal, and oral routes. The compositions may be administered by any convenient route, for example by infusion or bolus injection, by absorption through epithelial or mucocutaneous linings (e.g., oral mucosa, vaginal, rectal and intestinal mucosa, etc.) and may be administered together with other biologically active agents. Administration can be systemic or local. In addition, the contrast agent(s) compositions may be introduced into the central nervous system by any suitable route, including intraventricular and intrathecal injection; intraventricular injection may be facilitated by an intraventricular catheter, for example, attached to a reservoir, such as an Ommaya reservoir. The compositions of the invention can be delivered by any means known in the art systematically (e.g. intravenously), regionally or locally (e.g. intra- or peri-tumoral or intra-cystic injection, e.g. to image bladder cancer) by e.g. intra-arterial, intra-tumoral, intra-venous (iv), parenteral, intra-pneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs). For example intra-hepatic artery injection or intra-carotid artery injection may be used. If it is decided to deliver the preparation to the brain, it can be injected into a carotid artery or an artery of the carotid system of arteries (e.g. ocipital artery, auricular artery, temporal artery, cerebral artery, maxillary artery etc.). The present invention also provides pharmaceutical compositions which include contrast agents, alone or with a pharmaceutically acceptable carrier.

In some embodiments, amounts of the contrast agents sufficient to provide the desired results will be used, balanced by other considerations such as whether the contrast agent used for a particular application might produce undesirable physiological results. In some embodiments, the precise dose to be employed in the formulation can also depend on the route of administration, and should be decided according to the judgment of the practitioner and each subject's circumstances. In addition, in vitro and in vivo assays may optionally be employed to help identify optimal dosage ranges. Effective doses may be extrapolated from dose-response curves derived from in vitro or in vivo test systems. In some embodiments, the amounts of the contrast agent or agents administered can range from micromolar to molar amounts, but more likely will be used in millimolar-to-micromolar amounts.

The formulations of the invention can be administered in a variety of unit dosage forms, depending upon the particular cell or tissue or cancer to be imaged, the general medical condition of each patient, the method of administration, and the like. Details on dosages are well described on the scientific and patent literature. The exact amount and concentration of contrast agent or pharmaceutical of the invention and the amount of formulation in a given dose, or the "effective dose" can be routinely determined by, e.g. the clinician. The "dosing regimen" will depend upon a variety of factors, e.g. whether the cell or tissue or tumor to be imaged is disseminated or local, the general state of the patient's health, age and the like. Using guidelines describing alternative dosing regimens, e.g. from the use of other imaging contrast agents, the skilled artisan can determine by routine trials optimal effective concentrations of pharmaceutical compositions of the invention.

In some embodiments, the invention also provides a pack or kit comprising one or more containers filled with one or more of the ingredients of the contrast agent(s) compositions. In some embodiments, the pharmaceutical compositions, comprising the multimodal contrast agents of the present invention, may be administered in combination with other diagnostic or therapeutic treatments.

EXPERIMENTAL

Example 1

Synthesis of Core-shell $CoFe_2O_4@SiO_2$ Nanoparticles

The following example describes the design and synthesis of an exemplary $T_1$-$T_2$, multimodal MRI contrast agent, although the present invention is not limited to these particular compositions or synthesis methods.

A modified inverse micro-emulsion based sol-gel approach was used to fabricate stable and well-dispersed $CoFe_2O_4@SiO_2$ nanoparticles with improved control over shell thickness and core diameters. The $CoFe_2O_4$ core particles were synthesized according using the method of Sun et al. with slight modifications (Sun et al. *J. Am. Chem. Soc.* 2004, 126, 273-279, herein incorporated by reference in its entirety). A quantity of 40 mL of benzyl ether solution containing 2 mmol concentrated iron and cobalt acetylacetonate ($Fe(acac)_3$ and $Co(acac)$) was reduced by 10 mM hexadecanediol under N, blanket and heating at 275° C. to yield stable cobalt ferrite ($CoFe_2O_4$) nanoparticles in non-aqueous conditions. The solution was heated in presence of 6 mmol lauric acid and lauryl amine, which play the key role of surface stabilizers for the nanoparticles. The mixture turns brown after mixing at 100° C. and holding the mixture at this temperature for 30 min eliminates the water and other organic moistures. The solution turns dark brown indicating that nanoparticles are nucleated at 200° C.; however, holding the reaction mixture at this temperature for an hour homogenizes the nanoparticle growth during this time. By turning the temperature reaction around the boiling point of solvent (265-285° C.), it is observed that the rate of growth of nanoparticles is considerably enhanced and, consequently, all nanoparticle syntheses were carried out at this temperature The iron oxide nanoparticle solution was subjected to magnetic separation by ethanol precipitation, and the resulting aggregate was washed with copious amounts of ethanol and acetone to remove any uncoordinated stabilizer molecules. The aggregate was then dispersed in hexane for further studies.

The cobalt ferrite nanoparticles were coated with $SiO_2$ by base-catalyzed silica formation from tetraethylorthosilicate (TEOS) in a water-in-oil microemulsion (Lee et al. J. Phys. Chem. B 2006, 110, 11160-11166. and Deng et al. *Colloids Surf, A* 2005, 262, 87-93., herein incorporated by reference in their entireties) with slight modifications. IGEPAL CO-520 (1 mL) was mixed with 20 ml of anhydrous cyclohexane and stirred for 10 minutes. Cobalt ferrite nanoparticles were dispersed in cyclohexane at a concentration of 1 mg/mL and then poured slowly into the cyclohexane/Igepal solution. The amount of nanoparticle was adjusted so as to achieve desired silica shell thickness of approximately 10 nm. Then 120 µl of 30% $NH_4OH$ aqueous solution was added drop-wise and stirred for 15 minutes, followed by the addition of 190 µl of tetraethylorthosilicate. Depending on the desired silica shell thickness, the amount of TEOS can be varied. The mixture was stirred for 48 h before adding ethanol to precipitate the particles. The precipitate with ethanol was collected by centrifugation at 10,000 rpm and particles were washed by redispersing in ethanol. The $CoFe_2O_4@SiO_2$ nanoparticles were washed using this procedure at least three times to remove excess surfactant The final product was stored as a toluene dispersion for further surface modification with 3-aminopropyl triethoxysilane (APTES) or 3-mercaptopropyl trimethoxysilane (MPTMS). The surface modification was carried out at room temperature after injecting 100 µl of APTES or MPTMS in 1 mg of $CoFe_2O_4@SiO_2$ toluene-nanoparticle dispersion. The mixture was stirred rigorously for 2-4 days. The precipitated mixture was rinsed copiously with absolute alcohol and later dispersed directly in water or DMSO.

Figure 2:
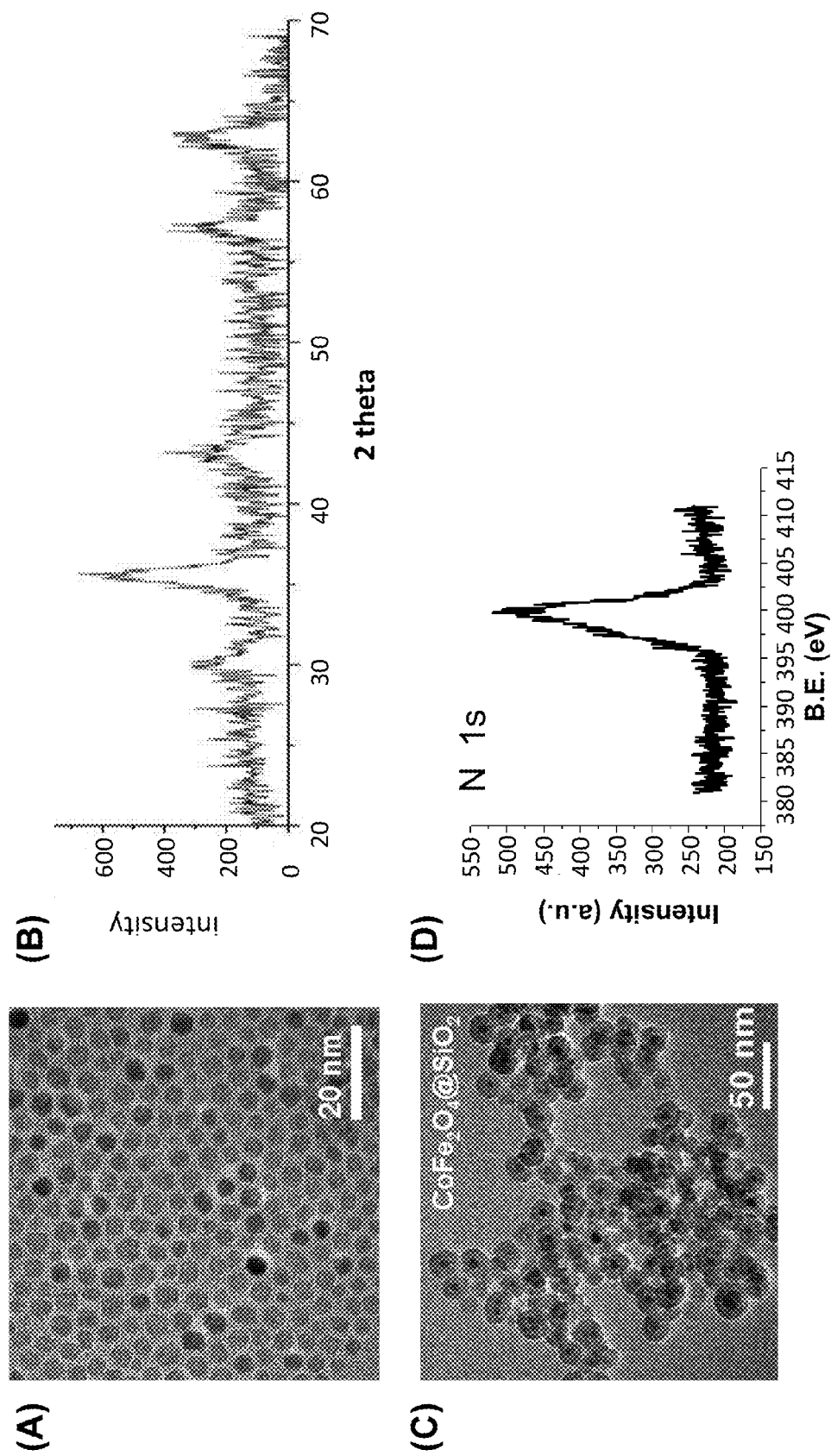
FIG. 2 shows analysis of nanoparticles: a) TEM image of $CoFe_2O_4$ nanoparticles, b) the XRD spectrum of $CoFe_2O_4$ nanoparticles, c) TEM image of silica coated cobalt ferrite nanoparticles revealing the dark center and homogeneous gray silica shell, d) X-ray phoyoelectron spectra of Nis and S 2s peaks indicating the monolayer adsorption of APTEM and MPTMS.

The core-shell nanoparticles were characterized by transmission electron microscopy (TEM), energy-dispersive spectroscopy, elemental mapping, and surface characterization techniques such as FTIR and x-ray photoelectron spectroscopy (XPS). The TEM analysis of the bare particles (SEE FIG. 2a) reveals the uniformity in shape and size (7 nm, Std deviation $\leqq$10%) XRD spectrum (SEE FIG. 2b) confirmed the cobalt ferrite phase formation and Debye-Scherer equation was used to calculate the particle size and found to be in good agreement with TEM results. The particle core size can be tuned from 7-20 nm by varying the surfactant concentration and seed-mediated growth process TEM of the initial silica-coated particles (SEE FIG. 2c) suggests that the 7 nm core is uniformly isolated in an individual shell (10 nm thickness). This silica shell can be tuned from 10 to 50 nm by varying the TEOS concentration.

The presence of anchoring sites on the nanoparticles for attachment of $T_1$ agents was shown by FTIR and XPS FTIR spectrum of core-shell particles ($CoFe_2O_4@SiO_2$) clearly shows the presence of hydroxyl groups on the silica shell by the peak at 940 $cm^{-1}$. These surface functional groups are treated with APTES or MPTMS in dry toluene to convert them to surface amine or thiol groups for further attachment of $T_1$ agent. The presence of amine or thiol monolayer was confirmed by XPS(N 1s peak BE-400 eV and S 2s peak at 2285 eV) (SEE FIG. 2d).

Example 2

Synthesis of Exemplary $T_1$ Contrast Agent

The following example describes the synthesis of an exemplary $T_1$ contrast agent.

Synthesis of [(2-{carboxymethyl-[2-(carboxymethyl-{[2-(pyridin-2-yldisulfanyl)ethylcarbamoyl]-methyl}-amino)-ethyl]-amino}-ethyl}-amino]-acetic acid (1, DTPA-SS-pyridyl)

{Bis-[2-(2,6-dioxo-morpholin-4-yl)-ethyl]-amino}-acetic acid (DTPA dianhydride) (200 g, 5.60 mmol) was dissolved in 100 mL of anhydrous DMSO and allowed to stir under a nitrogen atmosphere while S-(2-Aminoethylthio)-2-thiopyridine Hydrochloride (AETP) (0.672 g, 3.040 mmol) was dissolved in a stirring solution of anhydrous DMSO (25 mL) and anhydrous DIEA (1.067 g, 8.210 mmol). The AETP solution was slowly added to the DTPA dianhydride solution via syringe pump over 5 h. Upon complete addition, the resulting solution was stirred for an additional hour before being quenched with $H_2O$ (100 mL) and concentrated in vacuo. The resulting residue was brought up in $H_2O$ and submitted to preparatory HPLC with the Waters Atlantis column using the following method: ramp to 100% B over 35 min followed by a wash at 100% B for 5 min before returning to 0% B. The desired fractions (retention time: 10.28 min by UV at 235,280 urn) were collected and freeze dried to yield the product as a white solid.

Synthesis of gadolinium (III) [(2-{carborymethyl-[2-(carboxymethyl-{[2-(pyridin-2yldisulfanyl)-ethylcarbamoylJ-methyl}-amino)-ethylJ-amino}-ethyl)-aminoJ-acetic acid (2, Gd(III)DTPA-SS-pyritlyl)

DIPA-SS-pyridyl (500 mg, 0.089 mmol) was dissolved in 5 mL of $H_2O$, $GdCl_3$ (35.2 mg, 0013 mmol) was added to the solution and the pH was raised to 6.0 with NH$_4$OH. The resulting solution was stirred for 24 h at 40° C. and then cooled to RT. Raising the pH to 11.0 with NH$_4$OH caused the precipitation of unchelated gadolinium which was subsequently removed via filtration with a 0.2 um syringe filter. The resulting liquid was freeze dried to yield 555 mg of the product as a white solid (yield 89%).

Example 3

Figure 3:
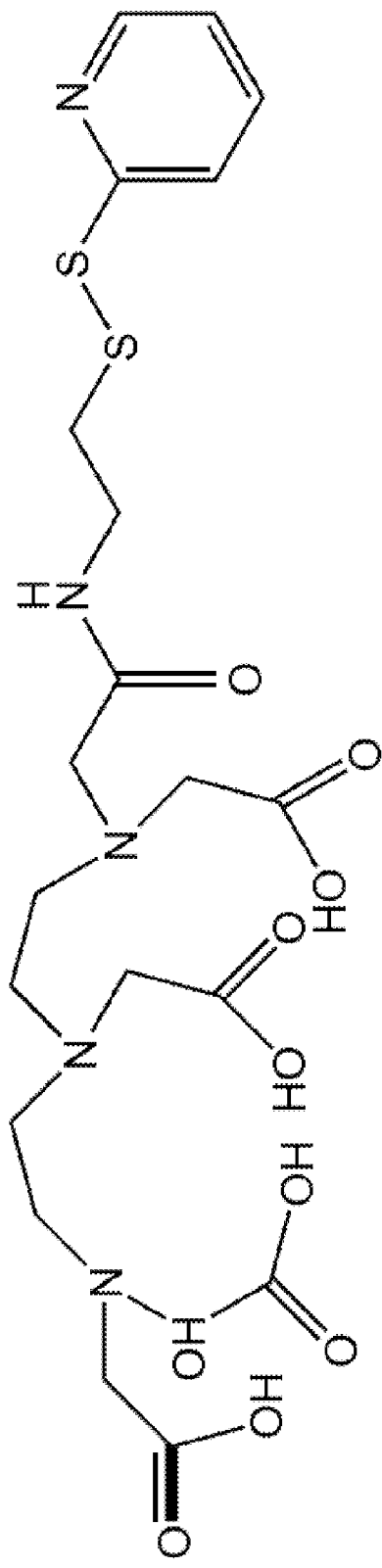
FIG. 3 shows structures of DTPA-SS-pyridyl (1) and Gd(III) DTPA-SS-pyridyl.
Figure 3:
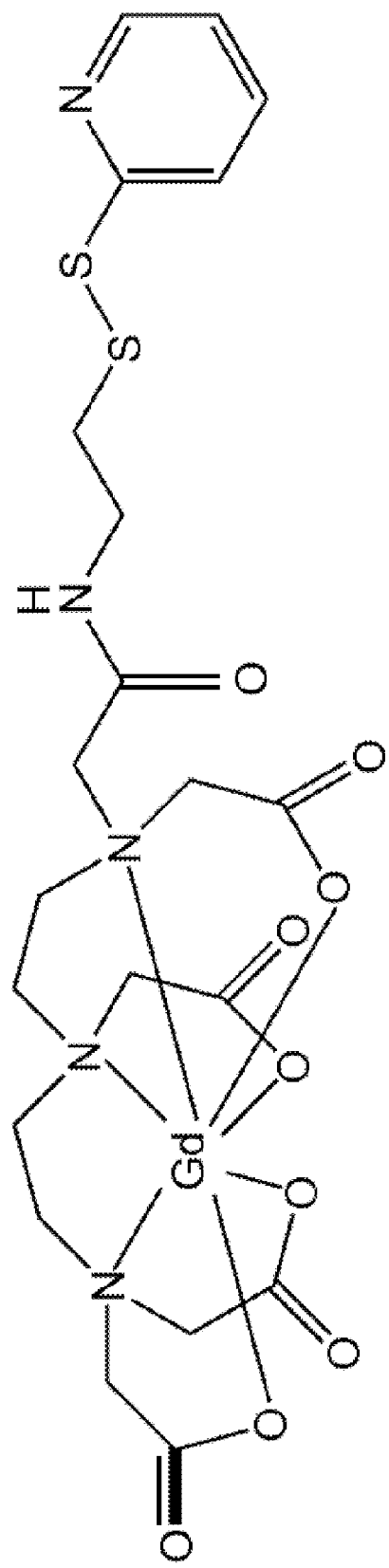

Synthesis of T$_1$-T$_2$ Contrast Agent, CoFe$_2$O$_4$@SiO$_2$—SS-DTPAGd(III), by Conjugation with Disulfide Linkage A 1.6 μmol Fe aliquot of CoFe$_2$O$_4$@SiO$_2$-thiol core-shell nanoparticles was added to 10 mM phosphate buffer pH 8 to give a concentration of approximately 1067 μM Fe. The solution was degassed and kept under N$_2$. A 9 μm aliquot of Gd(III) DTPA-SS-pyridyl (SEE FIG. 3) was dissolved in 200 μL 10 mM phosphate pH 8 buffer and added to the nanoparticle solution. The solution was degassed and reaction vessel filled with N$_2$. The reaction vessel was sealed and placed on a shaker at room temperature for 48 hours. After 24 hours, the pH was adjusted back into the reactive range using 100 mM NaOH. The agent was purified by dialysis against 10 mM phosphate pH 7.2 buffer followed by dialysis against water. Further purification was achieved using Millipore Amicon Ultra-4 30,000 MWCO centrifugal filter devices. HPLC-MS (Varian) and ICP (Varian) were used to monitor purification. The agent was characterized by ICP, dynamic light scattering (Malvern Instruments Zetasizer Nano Series), TEM-EDAX, and relaxivity (Bmker Minispec mq60 NMR Analyzer). The EDAX spectrum showed the presence of gadolinium, indicating successful conjugation of the paramagnetic Gd(III) chelate to the nanoparticle. Additionally, cobalt, iron, silicon, and sulfur are present. ICP analysis was used to determine the Gd:Fe ratio; these ratios are shown in Table 1. Following conjugation of the paramagnetic Gd(III) agent to the CoFe$_2$O$_4$@SiO$_2$-thiol particles, the stability in water of the T$_1$-T$_2$ agents decreased; therefore, to ensure accuracy, relaxation times were measured with samples embedded in 1% agarose gel. Relaxivity results are shown in Table 1. It is apparent from these results that the CoFe$_2$O$_4$@SiO$_2$ nanoparticles exhibited a drastic increase in transverse relaxivity (T$_2$) upon conjugation of the T$_1$ agent when using a spin echo sequence. The increase in transverse relaxivity of the T$_1$-T$_2$ agents was 2.1-3 times that of the T$_2$ agent alone. Changes in longitudinal relaxivity (rl) did not follow any trend. Moreover, when using a CPMG sequence to measure T$_2$ relaxation times, the resulting transverse relaxivity values did not follow a discernable trend. A control experiment, consisting of a mixture of unconjugated T$_1$ and T$_2$ agents, exhibited no change in relaxivity as compared to the T2 nanoparticles alone.

TABLE 1

Gd:Fe molar ratio and relaxivity for CoFeSiO$_x$—SH nanoparticles and multimodal CoFeSiO$_x$—Gd(III) nanoparticle agent.

| Sample | Gd:Fe | Relaxivity (mM$^{-1}$s$^{-1}$ Fe) | | Change in r$_2$ (%) |
| --- | --- | --- | --- | --- |
| | | r$_1$ | r$_2$ | |
| CoFeSiO$_x$—SH | N/A | 2.8 | 73.5 | N/A |
| CoFeSiO$_x$—Gd(III) | 0.049 | 8.0 | 219.1 | 198 |
| | 0.036 | 3.4 | 201.8 | 175 |
| | 0.031 | 2.6 | 152.3 | 107 |
| | 0.024 | 2.7 | 120.4 | 64 |
| | 0.013 | 2.7 | 94.8 | 29 |

Example 4

Gadolinium(III)-DTPA-Modified Cobalt Ferrite Nanoparticles

Figure 4:
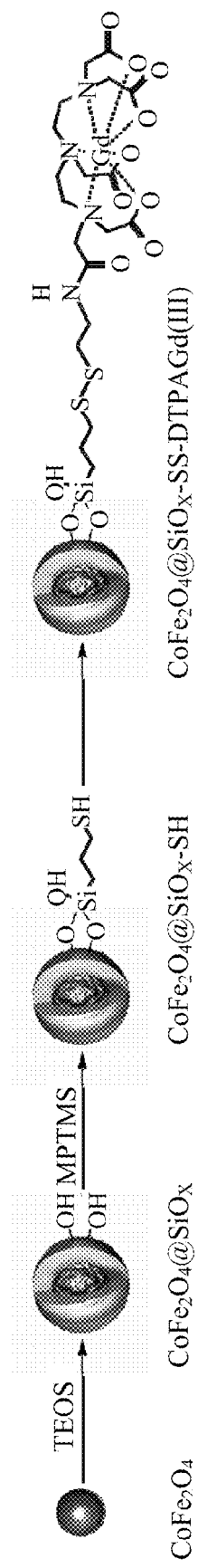
FIG. 4 shows an exemplary schematic of the preparation of multimodal $CoFeSiO_x$—Gd(III) nanoparticle agent.

In the following example, the design, synthesis, and characterization of the first example of a multimodal contrast agent, CoFeSiO$_x$—Gd(III), composed of a paramagnetic Gd(III)-DTPA derivative covalently attached to a SPM cobalt ferrite nanoparticle, is described. This system has the capability to co-localize and optimize imaging in two MR modalities (T$_1$ and T$_2$) with one contrast agent by improving the T$_2$ sensitivity of the SPM nanoparticle and administering high concentrations of Gd(III) to enhance T$_1$ signal. The magnetic interactions that occur between the paramagnetic and superparamagnetic entities, when covalently linked, were investigated during development of embodiments of the present invention. The covalent attachment of the Gd(III)-DTPA derivative to the SPM nanoparticle had a substantial effect on the magnetic properties. The versatility in functionalization and conjugation strategies available in this class of agent allow for specific modulation of both T$_1$ and T$_2$ signals in an MR image, as well as for detection and imaging of a variety of biological processes. An exemplary preparation of the multimodal CoFeSiO$_x$—Gd(III) nanoparticle agent is described herein (SEE FIG. 4); although the present invention is not limited to any single multimodal contrast agent composition, nor preparation strategy.

Thiol-modified silica-coated cobalt ferrite nanoparticles (CoFeSiO$_x$—SH) were prepared in three subsequent stages: 1) cobalt ferrite core synthesis, 2) silica shell formation, and 3) surface thiol functionalization; although the present invention is not limited to any single synthesis strategy. The cobalt ferrite cores were prepared through high-temperature non-hydrolytic thermal decomposition followed by silica coating using a modified base-catalyzed water-in-oil microemulsion sol-gel approach (Sun et al. *J. Am. Chem. Soc.* 2004, 126, 273-279., Deng et al., *Colloids Surf, A* 2005, 262, 87-93., Lee et al. *J. Phys. Chem. B* 2006, 110, 11160-11166; herein incorporated by reference in their entireties). Thiol functionalization was achieved through surface modification with (3-mercaptopropyl)trimethoxysilane (MPTMS). The final nanoparticles were characterized using TEM, XRD, FTIR, and XPS.

This approach resulted in controlled core diameter and silica shell thickness with core-shell nanoparticles highly dispersed in aqueous solution. TEM analysis of the CoFeSiO$_x$—SH nanoparticles revealed the uniformity in shape and size of the core (7 nm, std. dev.≦10%) and SiO$_x$ coating of approximately 10 nm (SEE FIG. 5). XRD confirmed cobalt ferrite phase formation and the particle sizes calculated by the Debye-Scherer equation were found to be in good agreement with TEM results. FTIR and XPS of the core-shell nanoparticles verified surface modification of the cobalt ferrite core with silica and MPTMS. The hydrodynamic size of the nanoparticles was determined to be 55±9 nm.

The Gd(III)-DTPA derivative was covalently anchored to the nanoparticle through a disulfide linkage between the —SH presented on the CoFeSiO$_x$ nanoparticle surface and the 2-pyridyl-dithio group on Gd(III)-DTPA-SS-pyridyl yielding the multimodal probe, CoFeSiO$_x$—Gd(III); although the present invention is not limited to a single synthesis strategy. Extensive dialysis and size filtration by centrifugation were used to remove excess unbound Gd(III)-chelate. Following purification, size and metal composition of the agent was determined.

Figure 5:
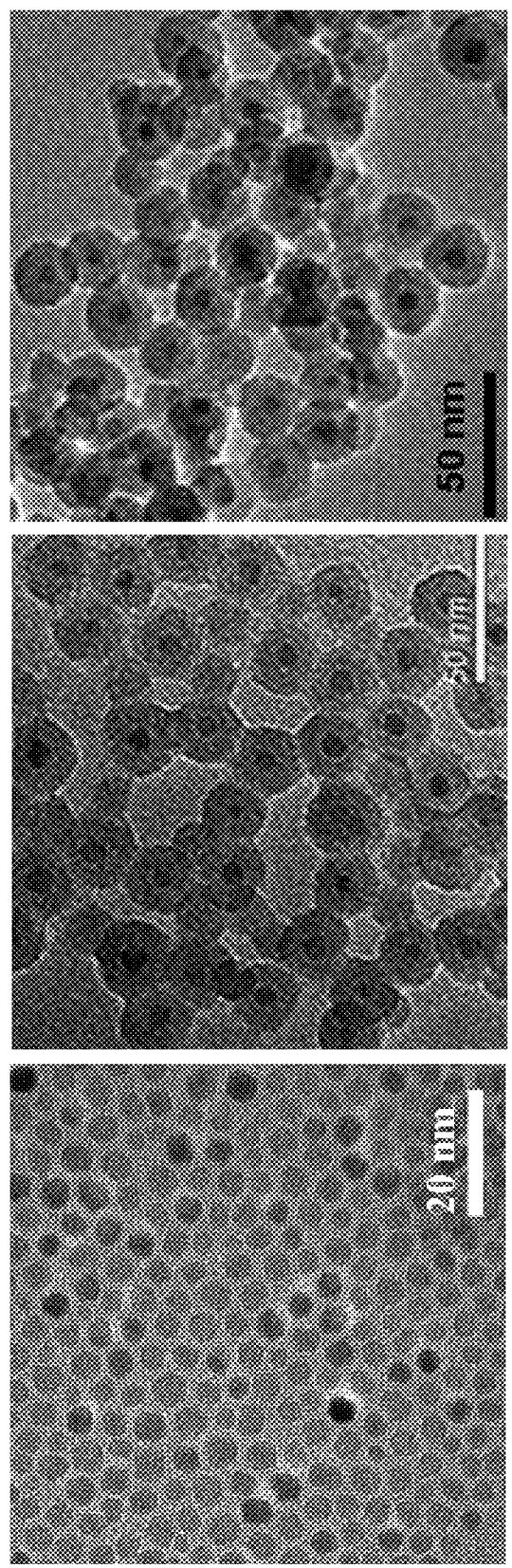
FIG. 5 shows TEM images of cobalt ferrite cores (left), $SiO_x$-coated cobalt ferrite core-shell nanoparticles (middle), and Gd(III)-DTPA-modified nanoparticles (right).

The morphological features of the silica-coated cobalt ferrite nanoparticles did not alter upon conjugation of Gd(III)-DTPA-SS-pyridyl as observed by TEM (SEE FIG. 5). EDS analysis showed the presence of Gd, Fe, Co, and S, which supports the successful attachment of Gd(III)-DTPA to the nanoparticle surface and illustrates the integrity of the nanoparticle. The hydrodynamic size (62±20 nm) revealed that upon conjugation of Gd(III)-DTPA-SS-pyridyl the hydrodynamic size increased only slightly indicating the CoFeSiO$_x$—Gd(III) nanoparticles are not aggregated in solution.

The Co, Fe, and Gd content of the nanoparticles was determined by ICP-MS. A molar ratio of Co:Fe was used to monitor the integrity of the nanoparticle core. The Co:Fe molar ratios remained relatively constant (~0.26 Co:Fe) pre- and post-conjugation demonstrating that the cobalt ferrite cores remain intact throughout the synthesis. The ratio of Gd:Fe was used to quantify the amount of covalently attached Gd(III)-DTPA and assess the extent of conjugation to the core-shell nanoparticle surface. The amount of covalently attached Gd(III)-DTPA-SS-pyridyl ranged from 0.013-0.049 Gd:Fe (Table 1). During the conjugation of the Gd(III)-DTPA and cobalt ferrite core-shell nanoparticles, a substantial excess of Gd(III)-DTPA-SS-pyridyl was added to provide maximum coverage. Covalent attachment of the Gd(III)-DTPA derivative was verified through the cleavage of the disulfide linker with dithiothreitol (DTT) and reduced glutathione (GSH).

Experiments were conducted during the development of embodiments of the invention to obtain relaxivity values, by embedding the samples in 1% agarose gel and measuring the $T_1$ and $T_2$ relaxation times at 60 MHz and 37° C. The relaxivity (re, n=1, 2) was determined by taking the slope of a plot of $1/T_n$ versus concentration. The $r_1$ and $r_2$ values for CoFeSiO$_x$—SH nanoparticles and the CoFeSiO$_x$—Gd(III) nanoparticles are displayed in Table 1. The unmodified nanoparticles had an $r_1$ of 2.8 mM$^{-1}$s$^{-1}$ Fe and $r_2$ of 73.5 mM$^{-1}$s$^{-1}$ Fe. Upon covalent attachment of the Gd(III)-DTPA chelate to the CoFeSiO$_x$—SH nanoparticles, the $r_2$ significantly increased. The percent change in $r_2$ ranged from 29-198% which corresponded to increasing amounts of attached Gd(III)-DTPA-SS-pyridyl. No clear trend was observed in the $r_1$, albeit with higher amounts of conjugated Gd(III)-DTPA the $r_1$ increased.

The major factor for the substantial increase in relaxivity of the CoFeSiO$_x$—Gd(III) contrast agent is the covalent attachment of paramagnetic Gd(III) chelate to the nanoparticle surface, although the present invention is not limited to any particular mechanism of action and an understanding of the mechanism of action is not necessary to practice the present invention. When unbound Gd(III)-DTPA was added to a solution of nanoparticles, no change in relaxivity was observed. Furthermore, covalent attachment of the diamagnetic chelate Y(III)-DTPA-SS-pyridyl resulted in no change in $r_1$ and $r_2$ confirming that the reaction conditions and modification of the nanoparticle surface are not responsible for relaxivity changes. SPM nanoparticles are excellent $T_2$ contrast agents because they create microscopic field gradients that shorten $T_2$ of the surrounding water protons. The attachment of Gd(III)-DTPA-SS-pyridyl may add to the magnetic inhomogeneity in the local environment and as a result cause even shorter $T_2$ relaxation times, although the present invention is not limited to any particular mechanism of action and an understanding of the mechanism of action is not necessary to practice the present invention. The increase in $r_1$ at higher Gd(III) concentrations may also be due to an increase in rotational correlation time of the Gd(III)-DTPA derivative when it is attached to the nanoparticle surface, although the present invention is not limited to any particular mechanism of action and an understanding of the mechanism of action is not necessary to practice the present invention. Studies have reported that covalently linking Gd(III) chelates to silica-coated quantum dots and silica nanoparticles slows the rotational tumbling rate of the chelate which increases the rotational correlation time (Gerion et al. *J. Phys. Chem. C* 2007, 111, 12542-12551., Yang et al. *Advanced Materials* 2006, 18, 2890-2894.; herein incorporated by reference in their entireties). The attachment of the chelate leads to an increase in $r_1$ by constraining the rotational motion of the chelate. Therefore, each individual Gd(III) ion contributes more to the overall relaxivity. The aforementioned unbound Gd(III)-DTPA control mixture corroborates this explanation since a similar change in relaxivity did not occur if the chelate was not covalently attached to the nanoparticle.

Figure 6:
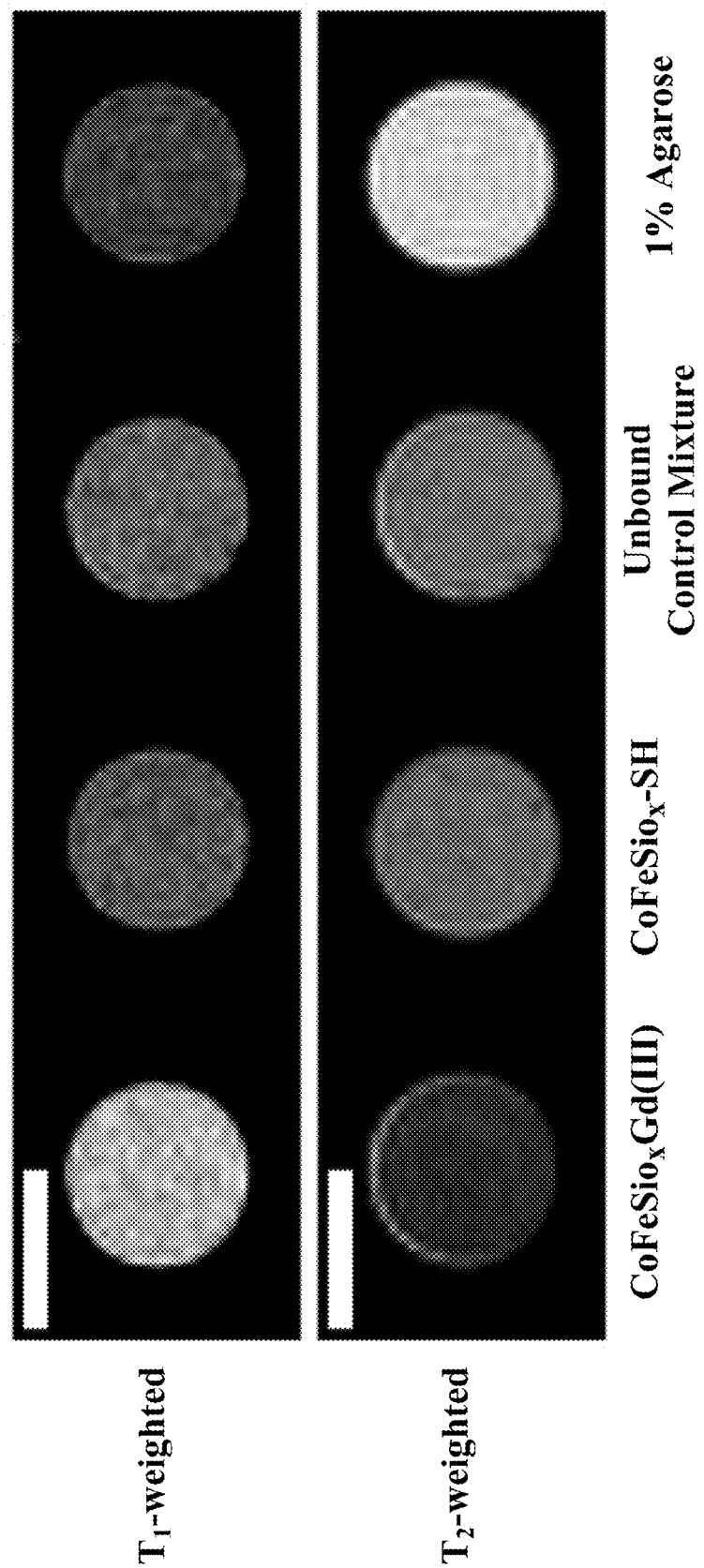
FIG. 6 shows in vitro MR phantom images at 200 MHz and room temperature using multi-slice multi-echo (MSME) pulse sequences. TR=500.0 ms and TE=14.6 ms for $T_1$-weighted images. TR=2000.0 ms and TE=30.0 ms for $T_2$-weighted images. Scale bars=2 mm.
Figure 7:
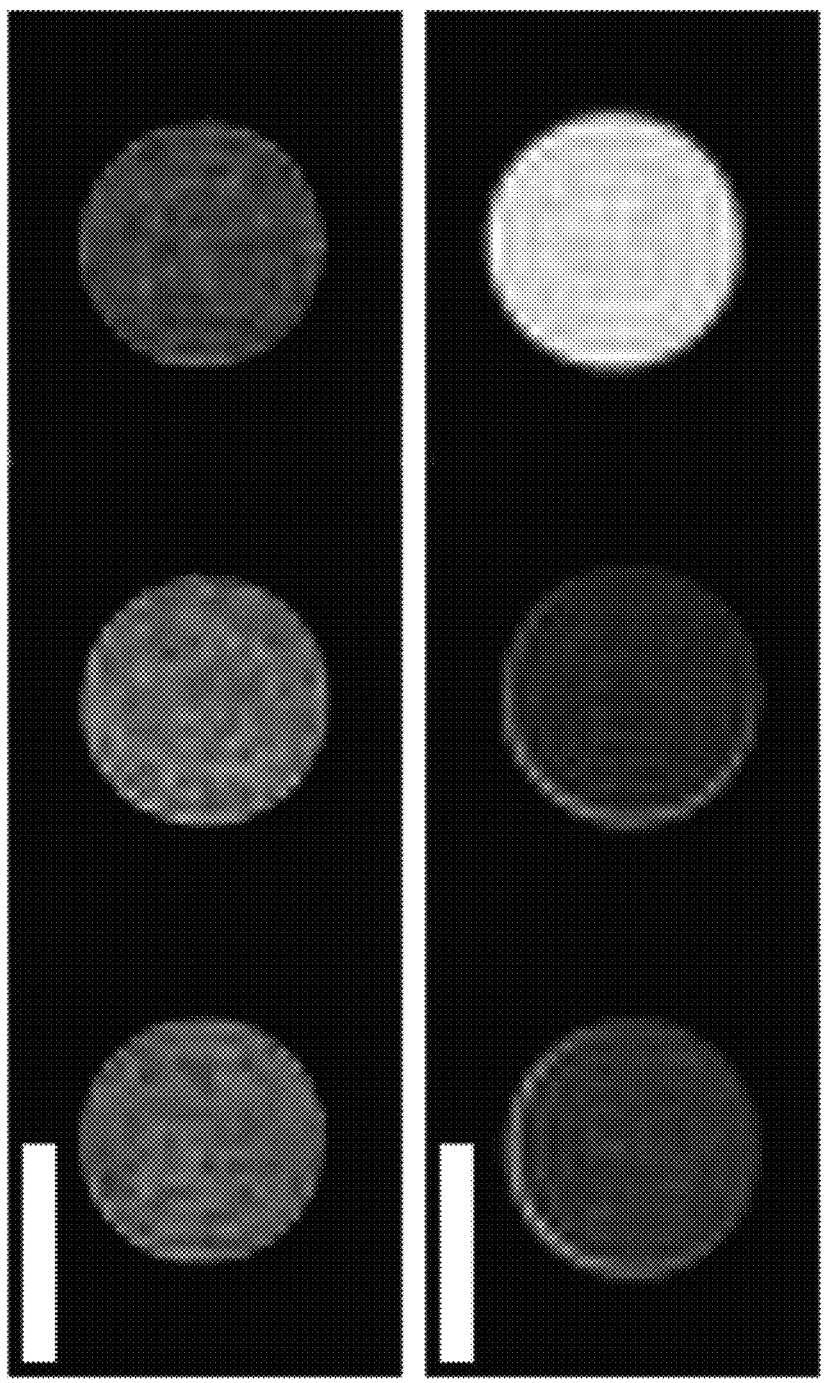
FIG. 7 shows In vitro MR phantom images at 200 MHz and room temperature using multi-slice multi-echo pulse sequences. TR=500.0 ms and TE=14.6 ms for $T_1$-weighted images. TR=2000.0 ms and TE=30.0 ms for $T_2$-weighted images. Scale bars=2 mm.

Experiments were conducted during the development of embodiments of the invention to determine whether the changes in relaxivity could be detected visually using MRI. Samples for in vitro MR phantoms were normalized by iron concentration and embedded in 1% agarose gel. Images were acquired at 4.7 T (200 MHz) and room temperature. Covalent attachment of Gd(III)-DTPA was visible at this field strength (SEE FIG. 6). The control samples exhibited no visible changes in intensity (SEE FIGS. 6 and 7). Using the same samples and imaging pulse sequences, $T_1$ and $T_2$ analysis was performed at 600 MHz and 25° C. The results at 600 MHz using imaging parameters corroborated the changes in $T_1$ and $T_1$ measured at 60 MHz. Based on the data obtained at 60, 200, and 600 MHz, the CoFeSiO$_x$—Gd(III) is a better contrast agent than the nanoparticles alone.

Superconducting quantum interference device (SQUID) magnetometry allows direct measurement of the magnetic properties of the contrast agent. The magnetic susceptibility properties of the CoFeSiO$_x$—SH nanoparticle and CoFeSiO$_x$—Gd(III) nanoparticle agent were measured using a SQUID magnetometer and are summarized in Table 2. All samples were dispersed in water and frozen under a nitrogen environment.

TABLE 2

Summary of magnetic susceptibility properties obtained by SQUID magnetometry.

| Sample | $T_B$ (K) | $H_C$ @ 5 K (kOe) | $H_C$ @ 250 K (kOe) | $M_s$ @ 5 K (emu/g core) | $M_s$ @ 250 K (emu/g core) |
|---|---|---|---|---|---|
| CoFeSiO$_x$—SH | 218 ± 2 | 17.3 | 0 | 74 ± 1 | 62 ± 1 |
| CoFeSiO$_x$—Gd(III) | 223 ± 2 | 18.6 | 0 | 61 ± 1 | 61 ± 1 |

Figure 8:
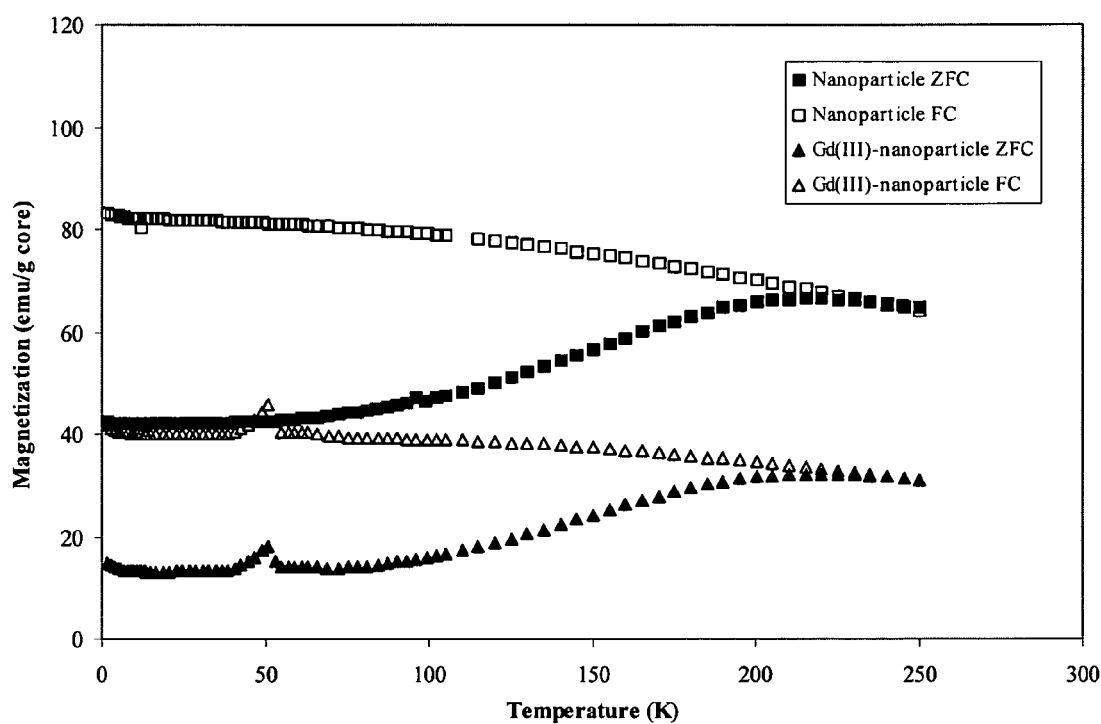
FIG. 8 shows ZFC (closed symbols) and FC (open symbols) curves of $CoFeSiO_x$ nanoparticles (squares) and $CoFeSiO_x$—Gd(III) nanoparticle agent (triangles).

Zero-field cooled (ZFC) and field cooled (FC) magnetization curves were obtained under an applied field of 500Oe (SEE FIG. 8). The peak of the ZFC curves represents the blocking temperature ($T_B$). The blocking temperatures for the CoFeSiO$_x$—SH nanoparticles and CoFeSiO$_x$—Gd(III) agent were found to be ~218 K and ~223 K, respectively. The ZFC and FC curves diverge significantly below T$_B$ indicating a ferrimagnetic state, while the curves coincide above T$_B$ confirming that both samples are in the superparamagnetic state (Huber *Small* 2005, 1, 482-501.; Vestal and Zhang. *Int. J. of Nanotechnology* 2004, 1, 240-263.; Lax and Button. *Microwave Ferrites and Ferrimagnetics*; McGraw-Hill Book Company, Inc.: New York, 1962.; herein incorporated by reference in their entireties). In the ZFC and FC curves for the CoFeSiO$_x$—Gd(III) nanoparticles, the peaks at approximately 51 K are a result of solid oxygen transformations and are not associated with any magnetic transition of the contrast agent (DeFotis. *Physical Review B* 1981, 23, 4714-4740.; herein incorporated in its entirety).

Figure 9:
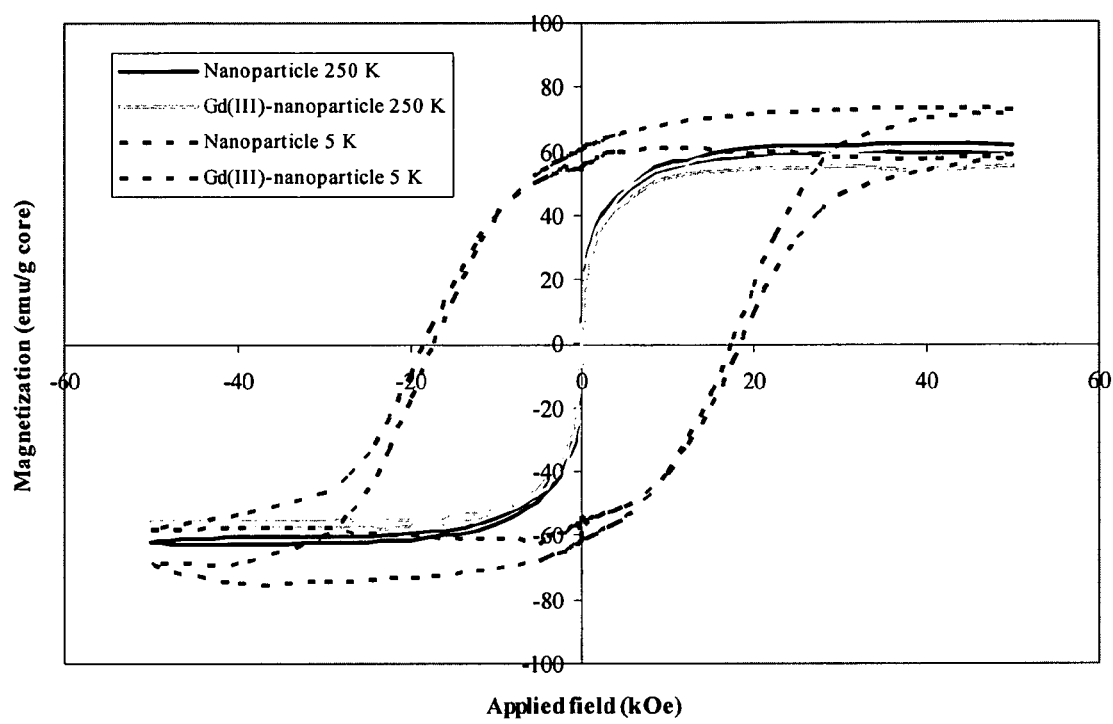
FIG. 9 shows magnetization vs. applied field at 5 K and 250 K for $CoFeSiO_x$ nanoparticles and $CoFeSiO_x$—Gd(III) nanoparticles.

Magnetization vs. applied magnetic field was measured at 5 K and 250 K for each sample (SEE FIG. 9). The coercivity (H$_x$) values for the CoFeSiO$_x$—SH and CoFeSiO$_x$—Gd(III) nanoparticles are 17.4 kOe and 18.5 kOe, respectively. The saturation magnetization (M$_x$) was found to be ~74 emu/g core for the CoFeSiO$_x$—SH nanoparticles and ~61 emu/g core for the CoFeSiO$_x$—Gd(III) nanoparticles. Additionally, both samples demonstrate high remanence. The non-zero coercivity and high remanence are characteristic of ferrimagnetic cobalt ferrites.[39,40] For example, 4 nm CoFe$_2$O$_4$ nanoparticles exhibited a ferrimagnetic coercivity of 10.3 kOe at 5 K. The larger values seen here are likely a result of the increased nanoparticle core size (7-8 nm).

Figure 10:
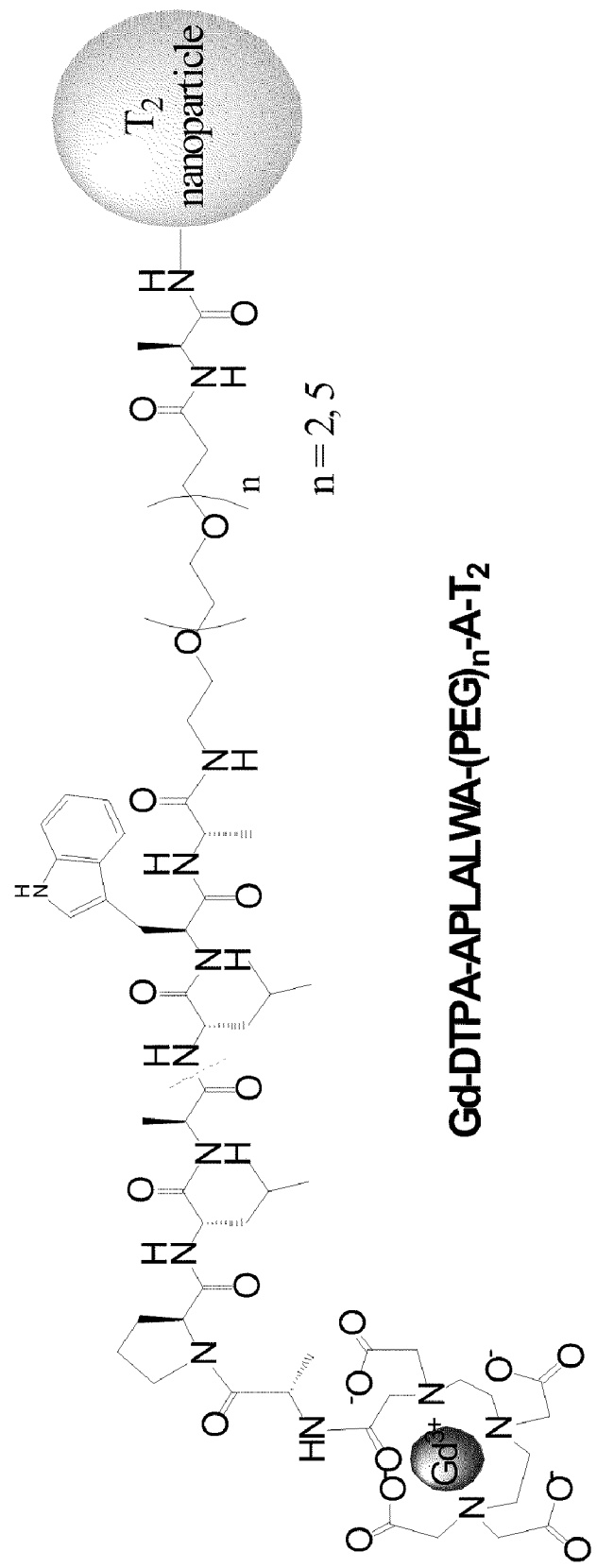
FIG. 10 shows an example of an enzyme-activated $T_1$-$T_2$ agent for the detection of MMP-7.

At 250 K, no coercivity and negligible remanence are observed showing that the agents are superparamagnetic above this temperature (SEE FIG. 10). The deviations in the field sweeps from negative to positive fields for both samples are a result of loss of water. The M$_s$ at 250 K was determined to be ~62 emu/g core and ~61 emu/g core for the unmodified nanoparticles and the CoFeSiO$_x$—Gd(III) agent, respectively.

Studies on the magnetic properties of lanthanides have shown that in heavy lanthanides, including Gd(III), the magnetic moments align antiferromagnetically and exhibit large magnetic anisotropies at low temperatures (Duc. *Handbook on the Physics and Chemistry of Rare Earths*, Elsevier: New York, 1997; Vol. 24, p 339-398.; Lin et al. *Physical Review B* 1990, 42, 2554-2557.; Jensen and Mackintosh. *Rare Earth Magnetism*; Oxford University Press: New York, 1991.; herein incorporated in their entireties).

In experiments performed during development of embodiments of the present invention, SQUID results indicate that the covalent attachment of Gd(III)-DTPA-SS-pyridyl has a significant impact on magnetic properties of the cobalt ferrite nanoparticles at low temperatures. For example, at 5 K, M$_s$ for the CoFeSiO$_x$—Gd(III) nanoparticle was significantly lower than the unmodified nanoparticles. It is contemplated that this occurs because the Gd(III) is antiferromagnetic and it disrupts the magnetism exhibited by the nanoparticle core, which results in a lower overall M$_s$; although the present invention is not limited to any particular mechanism of action and an understanding of the mechanism of action is not necessary to practice the present invention. In contrast, at 250 K the CoFeSiO$_x$—SH nanoparticles and CoFeSiO$_x$—Gd(III) nanoparticles are superparamagnetic and have the same M$_s$. Moreover, it is known that Gd(III) is paramagnetic at room temperature. Owing to the small amount of Gd(III)-DTPA conjugated to the nanoparticles, the paramagnetic contribution of the Gd(III) above T$_B$ is negligible when compared to the large superparamagnetism exhibited by the nanoparticles.

These results show that the Gd(III)-DTPA impacts the magnetic susceptibility of the cobalt ferrite nanoparticles significantly below the T$_B$.

Example 5

Figure 11:
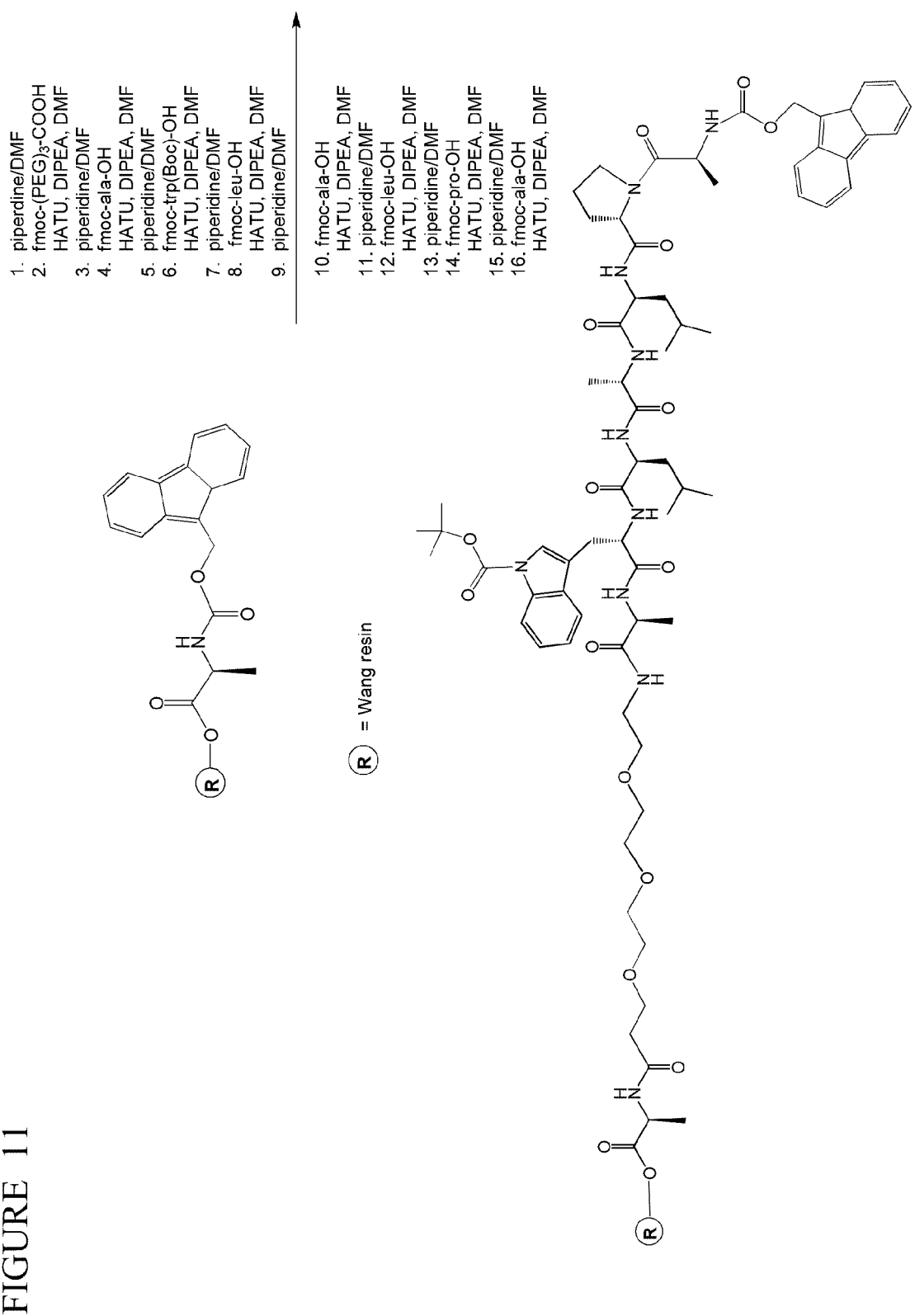
FIG. 11 shows a synthesis scheme of fmoc-Ala-Pro-Leu-Ala-Leu-Trp(Boc)-Ala-PEG$_3$-Ala-Wang resin.

Fmoc-Ala-Pro-Leu-Ala-Leu-Trp(Boc)-Ala-PEG$_3$-Ala-Wang Resin (SEE FIG. 11)

During development of embodiments of the present invention, peptides were synthesized according standard solid-phase peptide synthesis methods using manual batch-type synthesis and fmoc protected amino acids (Kates and Albericio, Solid-Phase Synthesis, A Practical Guide, Marcel Dekker, Inc, New York, N.Y., 2000.; herein incorporated by reference in its entirety).

During development of embodiments of the present invention, a Wang resin consisting of 100-200 mesh 1% cross-linked polystyrene beads functionalized with p-benzyloxybenzyl alcohol handle was used as a solid support for the stepwise addition of amino acids. The Wang resin was purchased (NovaBiochem, San Diego, Calif.) with the N-terminal amino acid, fmoc-alanine, preloaded onto the resin. The resin (1.09347 g, 0.68 mmol/g resin loading) was added to a fritted glass reactor vessel fitted with a 3-way valve for switching between N$_2$ (used to mix during all reactions and rinses) and vacuum (used to drain rinses and excess reactants). The dry Wang resin was pre-swelled with CH$_2$Cl$_2$ (1×10 minute rinse) followed by DMF (4×10 minute rinses). The N-terminal fmoc protecting group was removed using 20% piperidine in DMF (until determined >99% complete by the Kaiser test; typically 4×10 minutes). The resin was rinsed with DMF (4×10 minutes). The next amino acid (2.5 equivalents relative to the N-terminal amine on the amino acid attached to the Wang resin) to be added to the peptide was dissolved in a minimal amount of DMF. To this solution, HATU (2 equivalents) and DIPEA (5 equivalents) were added to form a yellow solution of the preactivated fmoc-amino acid. This solution was added to the resin and allowed to react while gently bubbling N$_2$ to mix the reactants until determined >99% complete (typically 2-12 hours) by the Kaiser test. Upon completion, the resin was rinsed with DMF (4×10 minutes). This process of fmoc removal and addition of the next amino acid was repeated for each amino acid until the desired sequence was obtained.

Example 6

Figure 12:
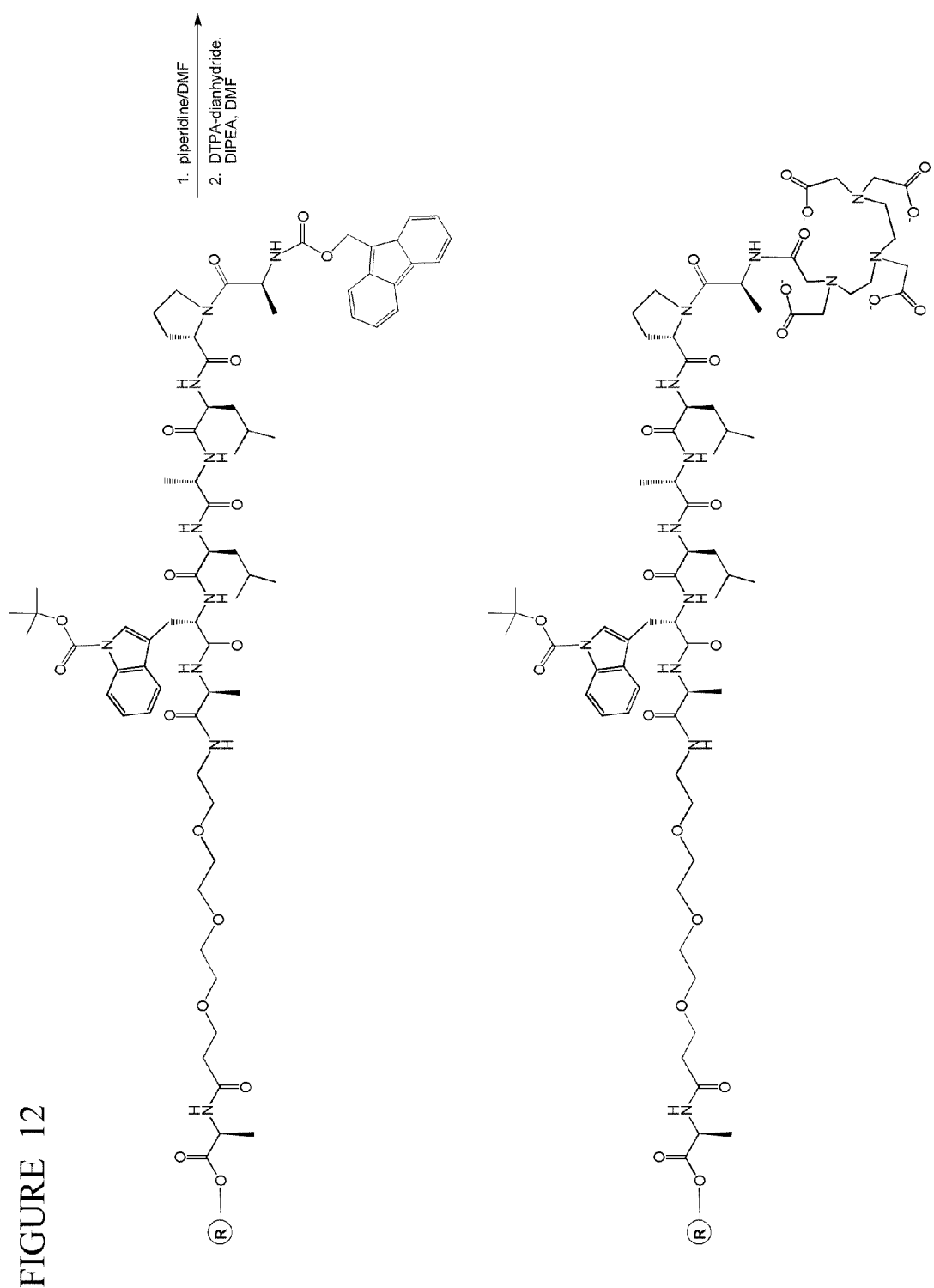
FIG. 12 shows a synthesis scheme of Diethylenetriaminepentaacetic acid-Ala-Pro-Leu-Ala-Leu-Trp(Boc)-Ala-PEG$_3$-Ala-Wang resin.

Diethylenetriaminepentaacetic Acid-Ala-Pro-Leu-Ala-Leu-Trp(Boc)-Ala-PEG$_3$-Ala-Wang Resin (SEE FIG. 12)

During development of embodiments of the present invention, the fmoc protecting group was removed from fmoc-Ala-Pro-Leu-Ala-Leu-Trp(Boc)-Ala-PEG$_3$-Ala-Wang resin as described in Example 11. Diethylenetriaminepentaacetic acid dianhydride (669.72 mg, 2.5 equivalents) was dissolved in a minimal amount of DMF using a few drops of anhydrous DMSO to aid solubility followed by addition of DIPEA (650 µL, 5 equivalents). This solution was added to the Wang resin and allowed to react until determined >99% complete (typically 2-4 hours) by the Kaiser test. After completion, the resin was rinsed with 1:1 DMF:H$_2$O (2×10 minutes) to hydrolyze the remaining anhydride of DTPA. The resin was rinsed with DMF (4×10 minutes), CH$_2$Cl$_2$ (4×10 minutes), methanol (4×10 minutes), then dried under vacuum overnight.

Example 7

Figure 13:
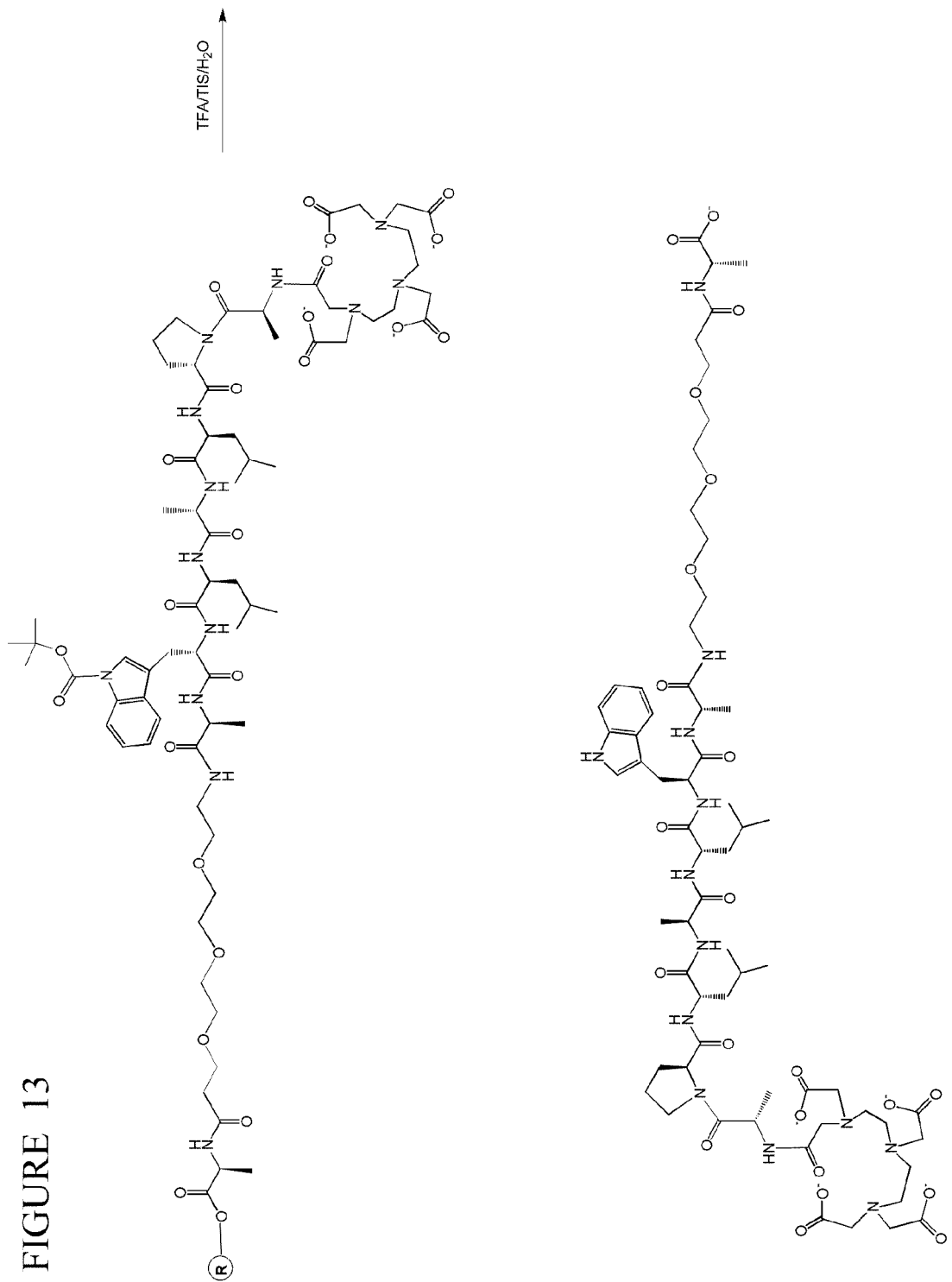
FIG. 13 shows a synthesis scheme of Diethylenetriaminepentaacetic acid-Ala-Pro-Leu-Ala-Leu-Trp-Ala-PEG$_3$-Ala.
Figure 14:
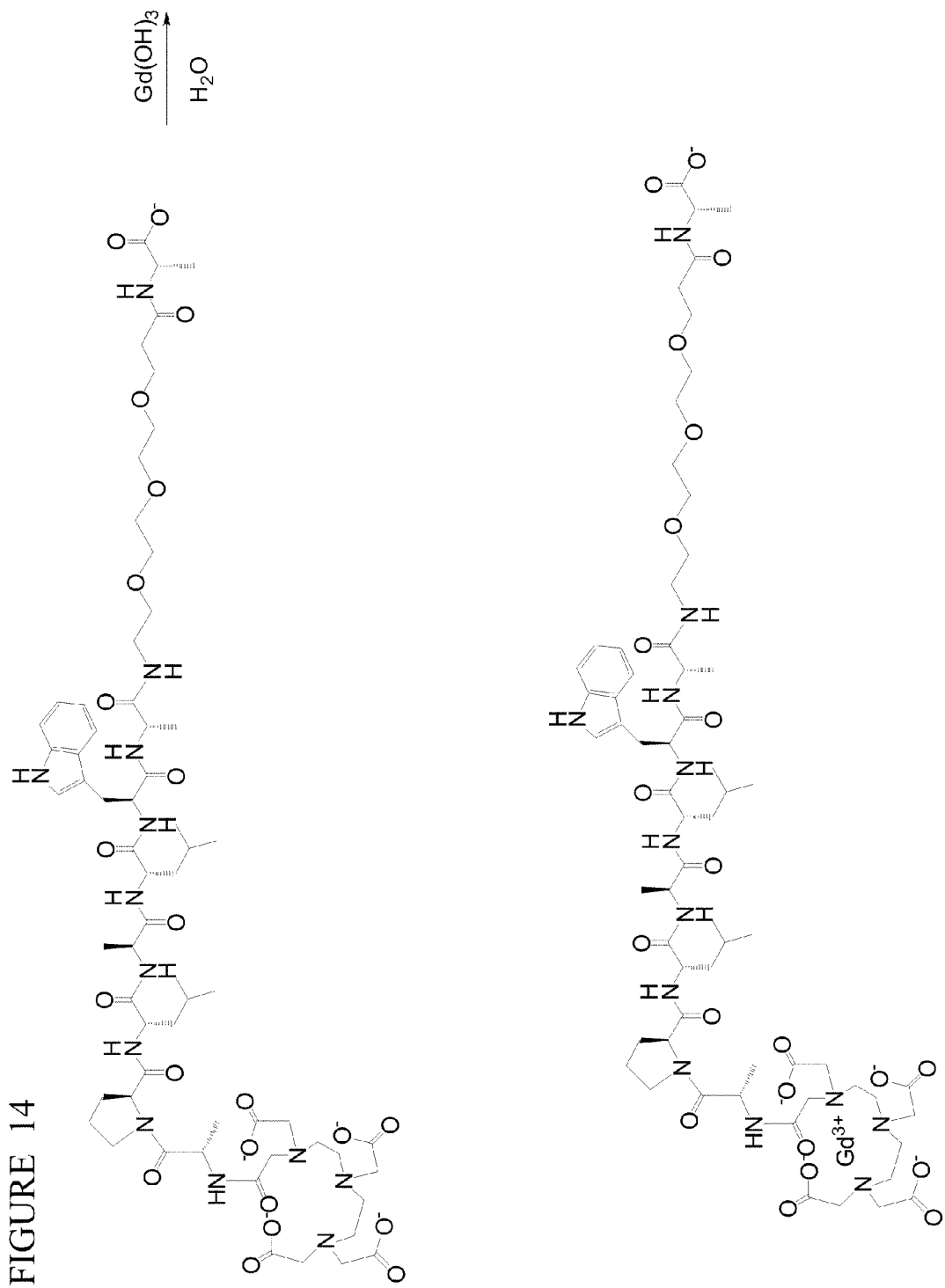
FIG. 14 shows a synthesis scheme of Gadolinium(III)-diethylenetriaminepentaacetic acid-Ala-Pro-Leu-Ala-Leu-Trp-Ala-PEG$_3$-Ala.

Diethylenetriaminepentaacetic Acid-Ala-Pro-Leu-Ala-Leu-Trp-Ala-PEG$_3$-Ala (SEE FIG. 13)

During development of embodiments of the present invention, a cleavage cocktail (15 mL) consisting of 95% TFA, 2.5% TIS, 2.5% H$_2$O was added to the dried Diethylenetriaminepentaacetic acid-Ala-Pro-Leu-Ala-Leu-Trp(Boc)-Ala-PEG$_3$-Ala-Wang resin. The resin was allowed to react in the cleavage cocktail for one hour, after which the solution was drained into a vial. Fresh cleavage cocktail (15 mL) was added to the resin and allowed to react for 10 minutes, followed by draining into a vial. Fresh cleavage cocktail (10 mL) was added to the resin and immediately drained into a vial. The cleavage cocktail solutions were combined and TFA was evaporated by passing N$_2$ over the vial. The volume was reduced to <1 mL followed by addition of cold (−20° C.) diethyl ether to precipitate the crude product as a white solid. The suspension was centrifuged and decanted. The diethyl ether extraction was repeated 4 times followed by evaporation of residual diethyl ether by passing N$_2$ over the vial. The white solid cake was dissolved in water (25 mL), frozen in liquid N$_2$, and lyophilized. The crude product was purified using preparative RP-HPLC (Solvent A=0.05% TFA in H$_2$O, Solvent B=MeCN; flow rate=15 mL/min; gradient starting at 0% B and ramping to 30% B over 5 minutes, hold isocratic 30% B for 15 minutes, ramp to 100% B over 3 minutes, hold isocratic 100% B for 5 minutes, ramp to 0% B over 5 minutes, hold isocratic 0% B for 7 minutes; fluorescence detection of tryptophan $\lambda_{ex}$=250 nm, $\lambda_{em}$=350 nm; UV/vis detection at 205 nm and 270 nm) by injecting sample (typically ~60 mg per injection) dissolved in water (3 mL, 0.22 µm filtered) with the desired product eluting at 13 minutes 45 seconds. MeCN was removed by rotary evaporation under reduced pressure. The remaining aqueous solution was frozen in liquid N$_2$ and lyophilized. Yield: 107.87 mg, 10% overall yield after 19 steps.

ESI-MS: calc. 1389.71; found positive mode 1390.68 (M+H), 1412.67 (M+Na$^+$); negative mode 1388.76 (M$^-$).

Example 8

Diethylenetriaminepentaacetic Acid-Ala-Pro-Leu-Ala-Leu-Trp-Ala-PEG$_6$-Ala

During development of embodiments of the present invention, a PEG$_6$ version was synthesized starting from 1.0001 g fmoc-ala-Wang resin (0.68 mmol/g resin loading) and purified (RP-HPLC retention time=14 minutes 30 seconds) using the same methods as described above by substituting the commercially available fmoc-PEG$_6$-COOH for fmoc-PEG$_3$-COOH. Yield: 106.54 mg, 10% overall yield after 19 steps.

ESI-MS: calc. 1521.78; found positive mode 773.09 (M+Na)$^{2+}$, 784.83 (M+2Na)$^{2+}$.

Example 9

Figure 18:
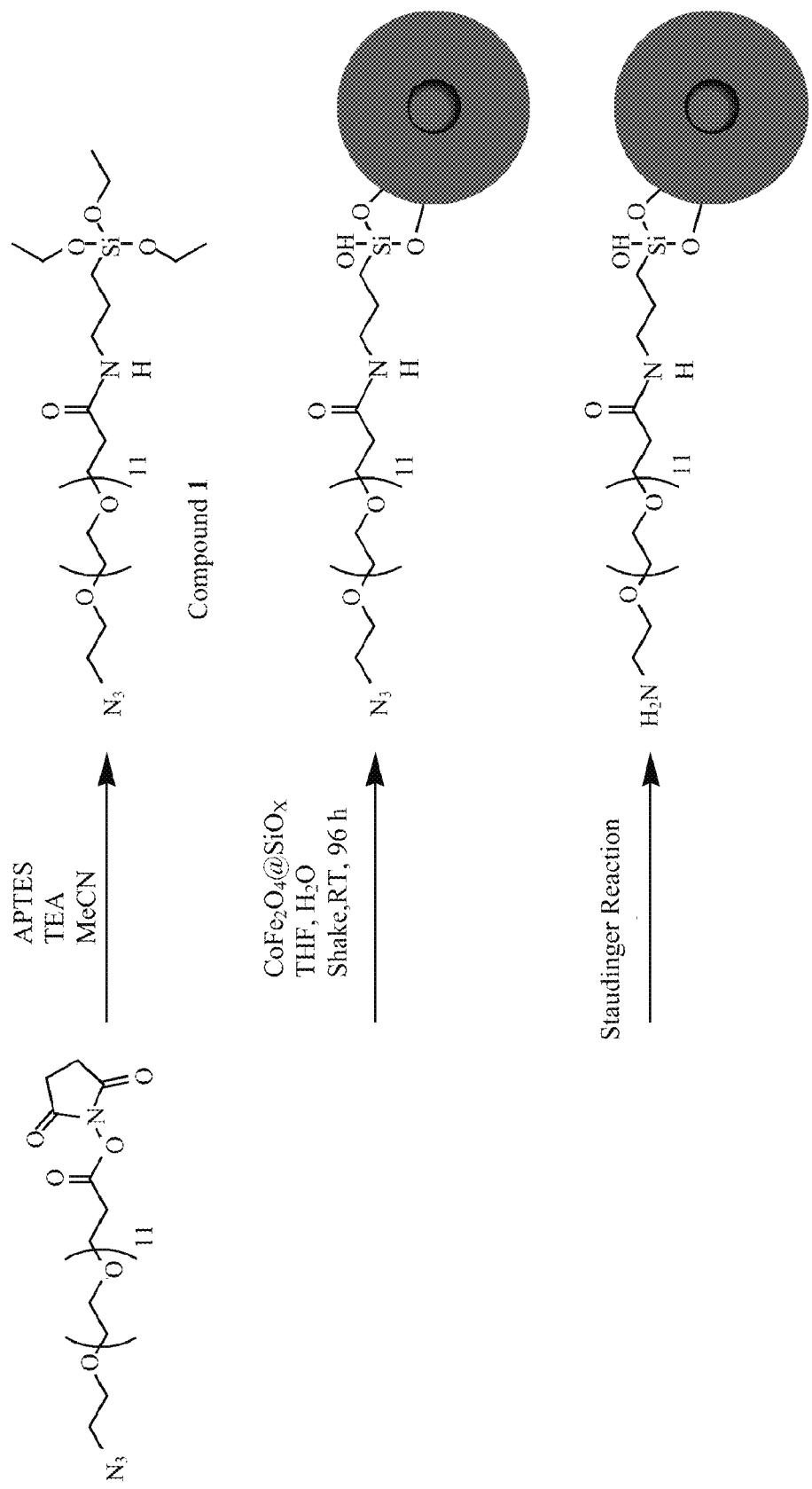
FIG. 18 shows a synthesis route for a stable nanoparticle for enzyme-activated $T_1$-$T_2$ agents, Route B.

Diethylenetriaminepentaacetic Acid-Ala-Pro-Leu-Ala (SEE FIG. 18)

During development of embodiments of the present invention, the cleaved version was synthesized starting from 1.365 g fmoc-ala-Wang resin (0.68 mmol/g resin loading) using the same methods as described above and purified (RP-HPLC retention time=9 minutes) using the same methods described above.

ESI-MS: calc. 745.35; found positive mode 746.80 (M+H)

$^1$H NMR (D$_2$O): δ=0.8, 0.9 (two sets of doublets, 6H, L$_\delta$, J=5.6 Hz); 1.4 (two sets of doublets, 6H, A$_\beta$, J=7.2 Hz); 1.5-1.6 (m, 3H, L$_\beta$ and L$_\gamma$); 1.8-2.3 (m, 4H, P$_3$ and P$_4$); 3.1-3.8 (m, 12H, DTPA CH$_2$CH$_2$, DTPA CH$_2$CONH, and P$_5$); 4.0, 4.1 (s, 8H, DTPA CH$_2$COOH); 4.2 (t, 1H, P$_\alpha$ or L$_\alpha$>, J=6.4); 4.3 (q, 1H, A$_\alpha$, J=7.2), 4.4 (t, 1H, P$_\alpha$ or L$_\alpha$, J=7.2), 4.6 (q, 1H, A$_\alpha$, J=7.2 Hz)

Example 10

Figure 15:
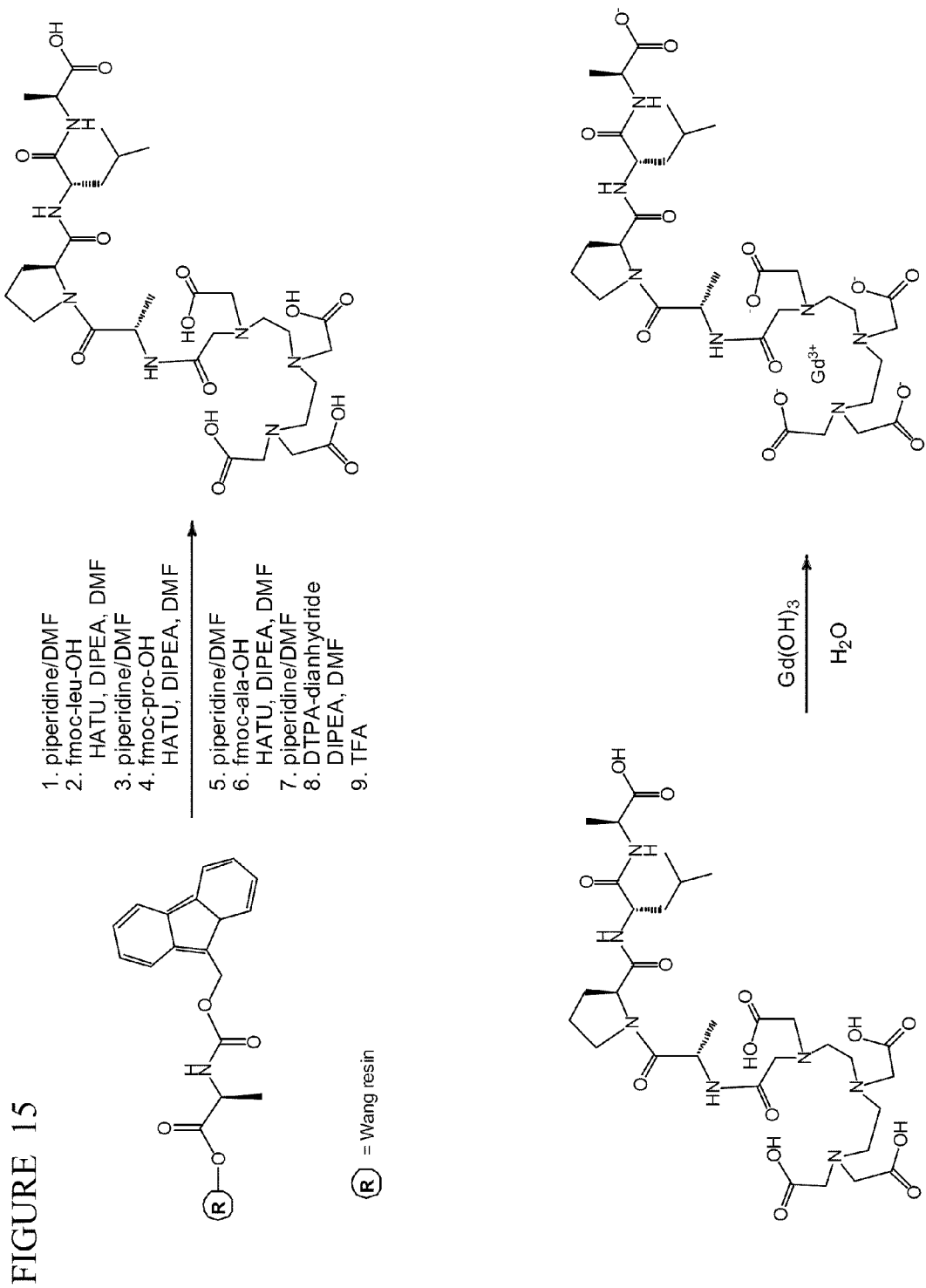
FIG. 15 shows a synthesis scheme of Gadolinium(III)-diethylenetriaminepentaacetic acid-Ala-Pro-Leu-Ala.

Gadolinium(III)-diethylenetriaminepentaacetic Acid-Ala-Pro-Leu-Ala-Leu-Trp-Ala-PEG$_3$-Ala (SEE FIG. 15)

During development of embodiments of the present invention, diethylenetriaminepentaacetic acid-Ala-Pro-Leu-Ala-Leu-Trp-Ala-PEG$_3$-Ala (54.20 mg, 0.03912 mmol) was placed in a 50 mL round bottom flask with magnetic stirbar and dissolved in 25 mL H$_2$O. The pH was adjusted to 5.5 using 5% NaOH followed by addition of Gd(OH)$_3$ (9.31 mg, 0.0295 mmol, 0.8 equivalents). The flask was capped with a rubber septum and sonicated briefly to reduce the size of the Gd(OH)$_3$ particulates before placing in a 80° C. oilbath with stirring. Over the course of the reaction, the pH gradually increased due to the release of OH$^-$ and there was a visible decrease in the amount of Gd(OH)$_3$ solids. The pH was periodically monitored and adjusted to 5.5 using HCl vapor. The reaction was determined to be complete when the pH ceased to change (usually 48-72 hours). The pH was raised to 10 using 20% NaOH (typically 2 µL) to precipitate any excess Gd$^{3+}$ as Gd(OH)$_3$ and 0.22 µm filtered. The filtrate was then frozen in liquid nitrogen and lyophilized. The crude product was purified using preparative RP-HPLC (Solvent A=H$_2$O, Solvent B=MeCN; flow rate=15 mL/min; same gradient as used above for Diethylenetriaminepentaacetic acid-Ala-Pro-Leu-Ala-Leu-Trp-Ala-PEG$_3$-Ala; fluorescence detection of tryptophan $\lambda_{ex}$=250 nm, $\lambda_{em}$=350 nm; UV/vis detection at 205 nm and 270 nm) by injecting sample dissolved in water (0.22 µm filtered) with the desired product eluting at 9.7 minutes (free ligand elutes at 11.0 minutes under these conditions). MeCN was removed by rotary evaporation under reduced pressure. The remaining aqueous solution was frozen in liquid N$_2$ and lyophilized. Yield: 39.01 mg, 86%.

ESI-MS: calc. 1542.75, found positive mode 784.43 (M+Na)$^{2+}$

MALDI-TOF MS: found positive mode 1544.8 (M+H$^+$), 1566.7 (M+Na$^+$), 1588.6 (M+2Na)$^+$, 1610.5 (M+3Na)$^+$. MS showed characteristic Gd isotope ratios.

Example 11

Gadolinium(III)-diethylenetriaminepentaacetic Acid-Ala-Pro-Leu-Ala-Leu-Trp-Ala-PEG$_6$-Ala During development of embodiments of the present invention, the PEG$_6$ version (52.76 mg, 0.03476 mmol) was metallated using Gd(OH)$_3$ (12.69 mg, 0.04011 mmol, 1.2 equivalents) and purified using the same methods as described for the PEG$_3$ version.

ESI-MS: calc. 1676.67; found positive mode 1743.65 (M+3Na)$^+$, 885.99 (M+4Na)$^{2+}$; negative mode 837.52 (m/2). MS showed characteristic Gd isotope ratios.

Example 12

Figure 16:
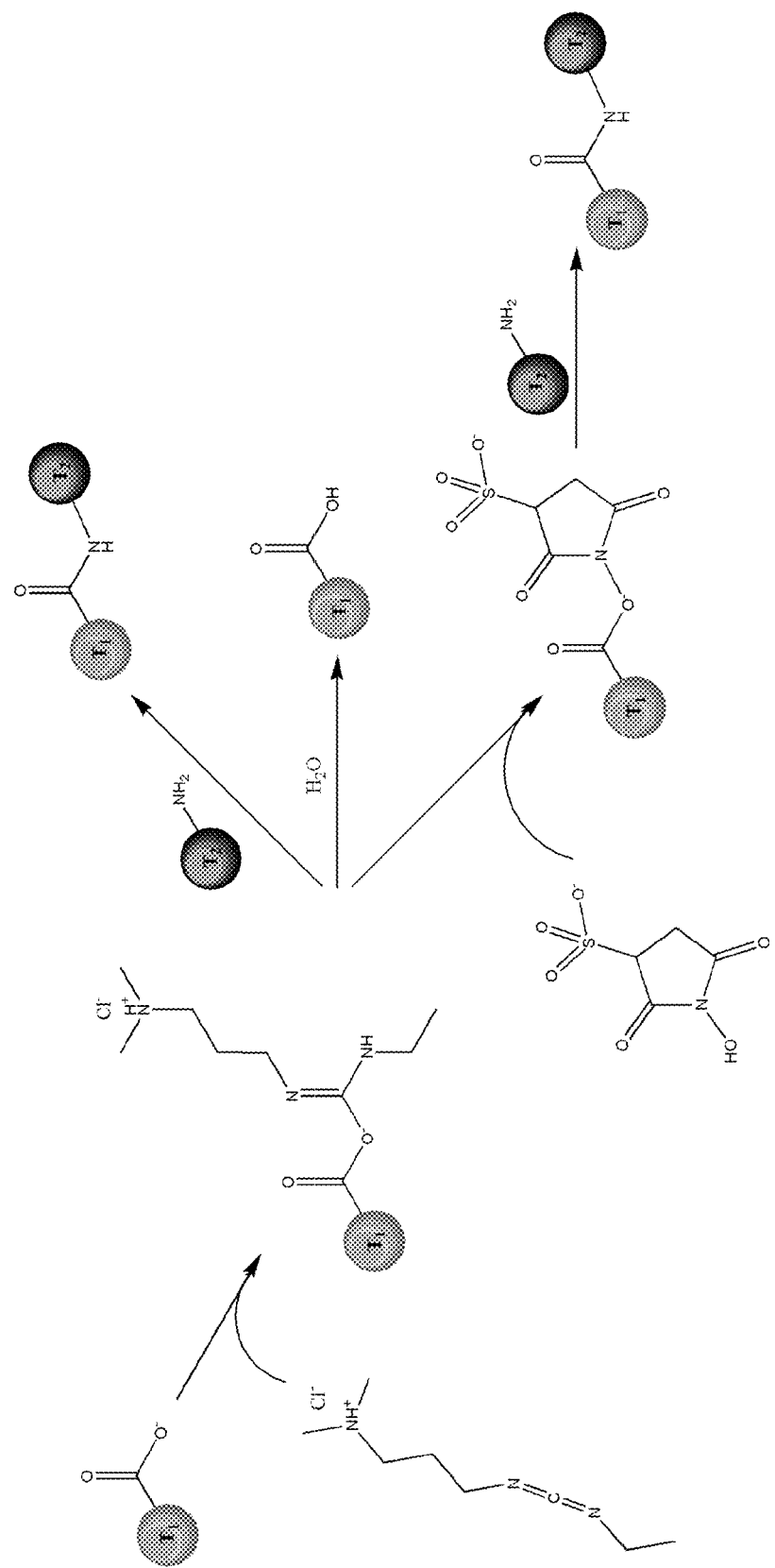
FIG. 16 shows the coupling of $T_1$ and $T_2$ agents using standard peptide coupling techniques with EDC and sulfo-NHS.

Gadolinium(III)-diethylenetriaminepentaacetic Acid-Ala-Pro-Leu-Ala (SEE FIG. 16)

During development of embodiments of the present invention, Diethylenetriaminepentaacetic acid-Ala-Pro-Leu-Ala (51.9 mg, 0.0696 mmol) was metallated using Gd(OH)$_3$ (24.2 mg, 0.766 mmol, 1.1 equivalents) using the same methods as described above.

ESI-MS: calc. 898.24; found positive mode Gd$^{3+}$ isotope pattern centered at 896.66 (M$^+$), 918.69 (M+Na$^+$).

Example 13

Enzymatic Cleavage

During development of embodiments of the present invention, a 2 μL aliquot of human recombinant MMP-7 was thawed on ice, diluted to 50 μL with assay buffer containing 1 mM APMA, and incubated for 1 hour at 37° C. to activate the enzyme. To the activated enzyme solution was added 1 μL of a 20 mM solution of gadolinium(III)-diethylenetriaminepentaacetic acid-Ala-Pro-Leu-Ala-Leu-Trp-Ala-PEG$_3$-Ala. The solution was incubated at 37° C. for 24 hours after which 10 μL was dissolved in 50 μL MeOH for analysis by ESI-MS. The mass spectrum revealed a peak corresponding to the MMP-7 cleavage fragment Leu-Trp-Ala-PEG$_3$-Ala [calc.: 662.35, found: positive mode 685.89 (M+Na$^+$)].

ESI-MS of a control solution lacking MMP-7 revealed only the expected uncleaved gadolinium(III)-diethylenetriaminepentaacetic acid-Ala-Pro-Leu-Ala-Leu-Trp-Ala-PEG$_3$-Ala [calc. 1542.75; found negative mode 771.60, (m/2)]

Example 14

Core-shell CoFe$_2$O$_4$@SiO$_2$ Nanoparticles

During development of embodiments of the present invention, a modified inverse micro-emulsion based sol-gel approach was used to fabricate stable and well-dispersed magnetic CoFe$_2$O$_4$@SiO$_2$ nanoparticles with improved control over shell thickness and core diameters. The CoFe$_2$O$_4$ core particles were synthesized according using the method of Sun et al. with slight modifications (Sun, et al., J Am Chem Soc 2004, 126:273-279, herein incorporated by reference in its entirety). A quantity of 40 mL of benzyl ether solution containing 2 mmol concentrated iron and cobalt acetyl acetonate (Fe(acac)$_3$ and Co(acac)$_3$) was reduced by 10 mM hexadecanediol under N$_2$ blanket and heating at 275° C. to yield stable cobalt ferrite (CoFe$_2$O$_4$) nanoparticles in non-aqueous conditions. The solution was heated in presence of 6 mmol lauric acid and lauryl amine which play the key role of surface stabilizers for the nanoparticles. The mixture turns brown after mixing at 100° C. and holding the mixture at this temperature for 30 min eliminates the water and other organic moistures. The solution turns dark brown indicating that nanoparticles are nucleated at 200° C.; however, holding the reaction mixture at this temperature for an hour homogenizes the nanoparticle growth during this time. By turning the temperature reaction around the boiling point of solvent (265-285° C.), it is observed that the rate of growth of nanoparticles is considerably enhanced and, consequently, all nanoparticle syntheses were carried out at this temperature. The iron oxide nanoparticle solution was subjected to magnetic separation by ethanol precipitation, and the resulting aggregate was washed with copious amounts of ethanol and acetone to remove any uncoordinated stabilizer molecules. The aggregate was then dispersed in hexane for further studies.

The cobalt ferrite nanoparticles were coated with SiO$_2$ by base-catalyzed silica formation from tetraethylorthosilicate in a water-in-oil microemulsion, using the methods of Lee et al. and Deng et al. with slight modifications. Igepal CO-520 (1 mL) was mixed with 20 ml of anhydrous cyclohexane and stirred for 10 minutes. Cobalt ferrite nanoparticles were dispersed in cyclohexane at a concentration of 1 mg/mL and then poured slowly into the cyclohexane/Igepal solution. The amount of nanoparticle was adjusted so as to achieve desired silica shell thickness of approximately 10 nm. Then 120 μl of 30% NH$_4$OH aqueous solution was added dropwise and stirred for 15 minutes, followed by the addition of 190 μl of tetraethylorthosilicate (TEOS). Depending on the desired silica shell thickness, the amount of TEOS can be varied. The mixture was stirred for 48 h before adding ethanol to precipitate the particles. The precipitate with ethanol was collected by centrifugation at 10,000 rpm and particles were washed by redispersing in ethanol. The CoFe$_2$O$_4$@SiO$_2$ nanoparticles were washed using this procedure at least three times to remove excess surfactant. The final product was stored as a toluene dispersion for further surface modification with 3-aminopropyl triethoxysilane (APTES). The surface modification was carried out at room temperature after injecting 100 μl of APTES in 1 mg of CoFe$_2$O$_4$@SiO$_2$ toluene-nanoparticle dispersion. The mixture was stirred rigorously for 2-4 days. The precipitated mixture was rinsed copiously with absolute alcohol and later dispersed directly in water or DMSO.

The core-shell nanoparticles were characterized by transmission electron microscopy (TEM), energy-dispersive spectroscopy, elemental mapping, and surface characterization techniques such as FTIR and x-ray photoelectron spectroscopy (XPS). The TEM analysis of the bare particles reveals the uniformity in shape and size (7 nm, Std. deviation ≦10%). XRD spectrum confirmed the cobalt ferrite phase formation and Debye-Scherer equation was used to calculate the particle size and found to be in good agreement with TEM results. The particle core size can be tuned from 7-20 nm by varying the surfactant concentration and seed-mediated growth process. TEM of the initial silica-coated particles suggests that the 7 nm core is uniformly isolated in an individual shell (10 nm thickness). This silica shell can be tuned from 10 to 50 nm by varying the TEOS concentration.

The presence of anchoring sites on the nanoparticles for attachment of T$_1$ agents was shown by FTIR and XPS. FTIR spectrum of core-shell particles (CoFe$_2$O$_4$@SiO$_2$) clearly shows the presence of hydroxyl groups on the silica shell by the peak at 940 cm$^{-1}$. These surface functional groups are treated with APTES or MPTMS in dry toluene to convert them to surface amine or thiol groups for further attachment of T$_1$ agent. The presence of the amine monolayer was confirmed by XPS(N 1s peak BE ~400 eV).

Example 15

Covalent Attachment of Gd(III)-DTPA-APLALWA-PEG$_n$-A to Nanoparticle Surface During development of embodiments of the present invention, the synthesis of silica-coated cobalt ferrite core-shell nanoparticles (CoFe$_2$O$_4$@SiO$_2$) modified at the surface with 3-aminopropyltriethoxysilane (APTES). Standard peptide coupling techniques were used to covalently attach the C-terminus of the Gd(III)-DTPA-APLALWA-PEG$_n$-A peptide (n=3-6) to the amine groups on the surface of the APTES-modified nanoparticle (SEE FIG. 10). Briefly, 1-ethyl-3-[3-dimethylaminopropyl]carbodiimide hydrochloride (EDC, 4.2 µmol) and N-hydroxysulfosuccinimide (sulfo-NHS, 4.2 µmol) were dissolved in 100 µL DMSO and 50 µL 100 mM MES pH 6.2. Gd(III)-DTPA-APLALWA-PEG$_n$-A (0.8 µmol) was dissolved in 100 µL DMSO and added to the solution of EDC and sulfo-NHS. The reaction was incubated at room temperature for 15 minutes and subsequently added to a solution of APTES-modified $CoFe_2O_4$@$SiO_2$ nanoparticles (0.7 µmol Fe) in DMSO. The reaction mixture was incubated at room temperature with end-over-end rotation for 24 h. Excess reagents were purified by extensive dialysis against a 5% DMSO in water mixture followed by size filtration using Millipore Amicon Ultra-4 100,000 MWCO centrifugal filter devices. ICP-MS was used to quantify the Co, Fe, and Gd content of the agents.

Various reaction conditions have been investigated in order to optimize the conjugation yield. Aqueous and organic solvents were tested and it was found that higher conjugation was achieved in polar aprotic solvents, namely DMSO. The coupling agents (EDC and sulfo-NHS) were added in 6-fold excess and preliminary data indicates that the addition of more equivalents of the coupling agents (up to 12) does not have as large of an effect on the yield as the solvent.

Example 16

Optimization of Stability of Multimodal MMP-7 $T_1$-$T_2$ Agent for Physiological Conditions Pre-conjugation the unmodified SPM nanoparticles are not stable in aqueous conditions. Post-conjugation the MMP-7 Gd(III)-modified nanoparticles exhibit slightly higher stability in aqueous conditions as compared to the unmodified nanoparticles. The increase in stability upon formation of the $T_1$-$T_2$ agent is favorable. A strategy to improve stability involves the introduction of a polyethylene glycol (PEG) moiety onto the nanoparticle surface prior to attachment of the Gd(III)-DTPA peptide derivative. Three synthetic routes for the synthesis of the amine-PEG$_{12}$ linker and the covalent attachment of the Gd(III)-DTPA peptide to the amine-PEG-nanoparticles are shown (SEE FIG. 17-19). Initially, a PEG$_{12}$ spacer is used; however, any length of the PEG spacer can be employed. Additionally, there are a variety of reaction parameters that can be modified in order to optimize the synthesis, including solvent, temperature, reagent concentration, and reaction time to list a few examples. Compounds 1 and 2 (described below) have been demonstrated as useful for use in the methods described herein.

Synthesis of azido-PEG$_{12}$-amidopropyltriethoxysilane (1). 3-aminopropyltriethoxysilane (APTES, 0.045 mmol) was added to a solution of azido-dPEG™$_{12}$-NHS ester (Quanta Biodesign, 0.051 mmol) in 30 mL anhydrous acetonitrile under a nitrogen atmosphere. Triethylamine (TEA, 0.029 mmol) was added to the reaction mixture to deprotonate the amine group of APTES. The solution was stirred for 24 h at room temperature. The solvent was removed by rotary evaporation under reduced pressure. Different polar aprotic solvents (e.g. THF) and bases (e.g. N,N-diisopropylethylamine, DIPEA) can be used for obtaining different yields.

Synthesis of amino-PEG$_{12}$-amidopropyltriethoxysilane (2). The azide group of compound 1 is reduced to an amine group in a solution of THF (or ethanol) under an atmosphere of $H_2$ at a pressure of 3 atm. Pd/C (10%) is used as a catalyst. The catalyst is removed by filtration and the solvent removed by rotary evaporation under reduced pressure. The crude mixture is either stored at −80° C. until further use or is immediately used to couple to the $CoFe_2O_4$@$SiO_2$ nanoparticles (Routes A-C described below).

Figure 17:
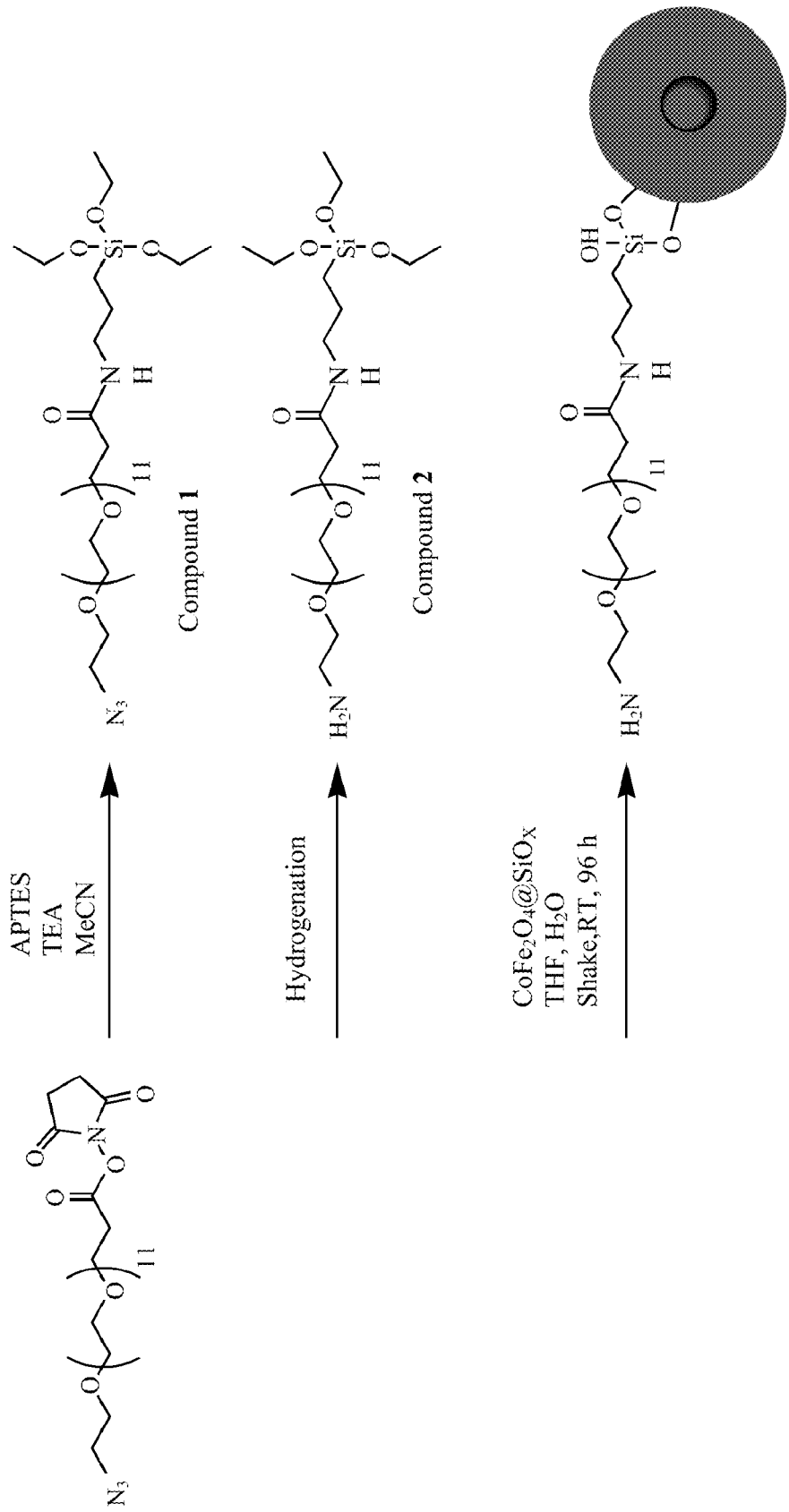
FIG. 17 shows a synthesis route for a stable nanoparticle for enzyme-activated $T_1$-$T_2$ agents, Route A.

Synthesis of amine-PEG-modified nanoparticles, Route A (SEE FIG. 17). Silica-coated cobalt ferrite nanoparticles in ethanol were precipitated with hexanes and redispersed in THF. The resulting solution was stable. Compound 2 is added to a solution of silica-coated cobalt ferrite nanoparticle solution. A small amount of water is added to catalyze the hydrolysis reaction. The reaction is placed on a shaker at room temperature for 96 h. Particles are isolated by a series of centrifuge/decant/resuspend cycles (5×) with ethanol/hexanes/THF or ethanol followed by dispersion directly in water, for example, although other purification approaches may be used. Further purification by size filtration is achieved using Millipore Amicon Ultra-4 100,000 MWCO centrifugal filter devices. The desired product is characterized by FTIR, Zeta potential, and dynamic light scattering (DLS). Other polar aprotic or protic solvents, such as DMSO, ethanol and water, and various temperatures may be used.

Synthesis of amine-PEG-modified nanoparticles, Route B (SEE FIG. 18). Compound 1 is added to a solution of silica-coated cobalt ferrite nanoparticles in THF. A small amount of water is added to catalyze the hydrolysis reaction. The reaction is placed on a shaker at room temperature for 96 h. Particles are isolated by a series of centrifuge/decant/resuspend cycles similar to that described in Route A. Following purification, the azide-PEG$_{12}$-modified nanoparticles is suspended in THF. The Staudinger reaction is used to convert the azide group to an amine group. Briefly, triphenylphosphine ($PPh_3$) is added to the nanoparticle/THF solution followed by the addition of $H_3PO_4$. The reaction mixture is stirred for 24 h. Purification of the amine-PEG$_{12}$-modified nanoparticles is performed in a similar manner as described in Route A.

Figure 19:
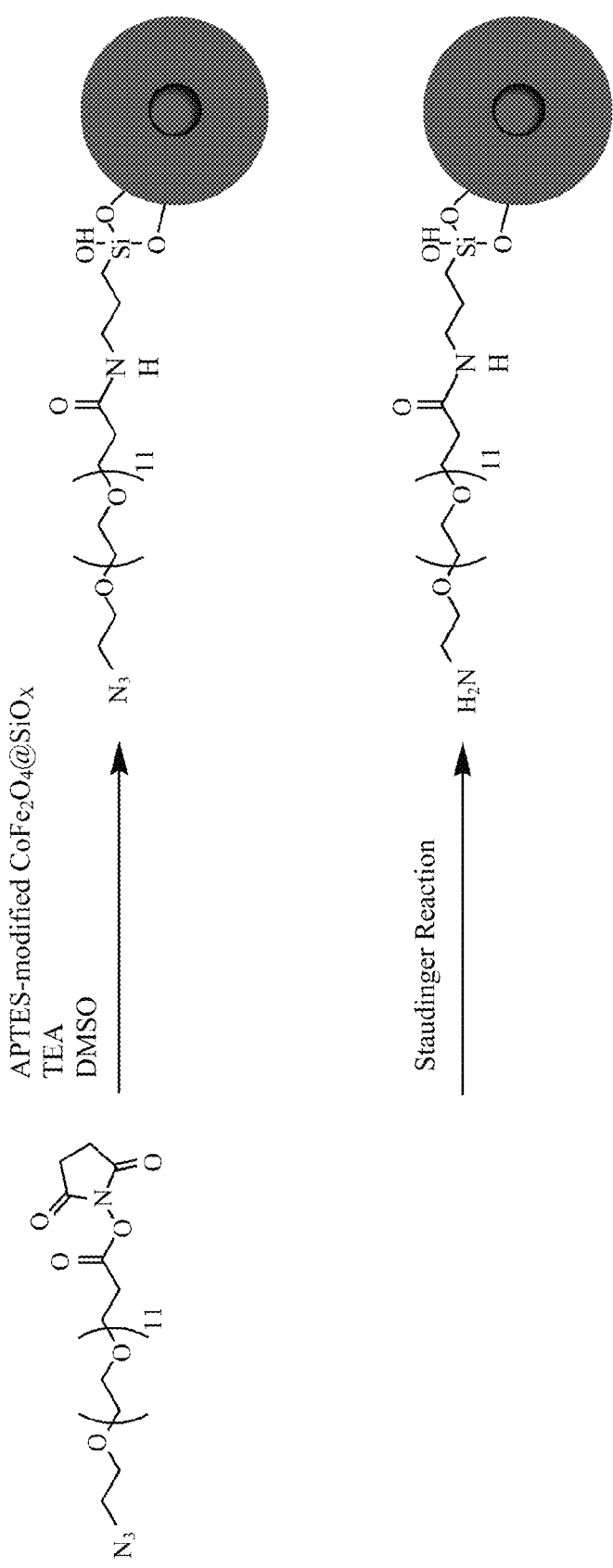
FIG. 19 shows a synthesis route for a stable nanoparticle for enzyme-activated $T_1$-$T_2$ agents, Route C.

Synthesis of amine-PEG$_{12}$-modified nanoparticles, Route C (SEE FIG. 19). Azido-dPEG™$_{12}$-NHS ester in anhydrous DMSO is added to a DMSO solution of APTES-modified silica-coated cobalt ferrite nanoparticles under a nitrogen atmosphere. TEA is added to the reaction mixture to deprotonate the amine groups on the nanoparticle surface. The solution is placed on a shaker for 24 h at room temperature. Different polar aprotic solvents (e.g. THF) and bases (e.g. N,N-diisopropylethylamine, DIPEA) may be used. Particles are isolated by a series of centrifuge/decant/resuspend cycles similar to that described in Route A. Following purification the azide-PEG$_{12}$-modified nanoparticles is dispersed in THF. The Staudinger reaction is used to convert the azide group to an amine group. Briefly, triphenylphosphine ($PPh_3$) is added to the nanoparticle/THF solution followed by the addition of $H_3PO_4$. The reaction mixture is stirred for 24 h. Purification of the amine-PEG$_{12}$-modified nanoparticles is performed in a similar manner as described in Route A.

Covalent attachment of Gd(III)-DTPA-APLAL WA-(PEG)$_n$-A to amine-PEG$_{12}$-modified nanoparticles. Gd(III)-DTPA-APLALWA-(PEG)$_n$-A is attached to the amine-PEG$_{12}$-nanoparticles following the procedure previously described for the attachment to APTES-modified nanoparticles. Additionally, a Gd(III)-DTPA-APLALWA agent (with no PEG spacer) can be attached to the amine-PEG$_{12}$-modified nanoparticles.

Example 17

Investigation of Relaxivity and Enzyme Activity of Multimodal MMP-7 $T_1$-$T_2$ Agent During development of embodiments of the present invention, experiments are performed to test the relaxivity and enzyme cleavage of these novel enzyme-activated multimodal $T_1$-$T_2$ contrast agents for MRI. A change in both longitudinal and transverse relaxivity ($r_1$ and $r_2$, respectively) should occur upon conjugation of the Gd(III)-DTPA peptide to the nanoparticle. Furthermore, upon cleavage of the peptide linker in the presence of the MMP-7 enzyme, another change in relaxivity is contemplated. A thorough investigation is performed on the following agents and controls: amine-PEG$_{12}$-modified CoFe$_2$O$_4$@SiO$_x$ nanoparticles ($T_2$ agent), Gd(III)-DTPA-APLALWA-(PEG)$_n$-A ($T_1$ agent), the conjugated enzyme-activated $T_1$-$T_2$ agent, a mixture of nanoparticles and Gd(III)-DTPA peptide agents that are not conjugated, and the Y(III) versions of all these samples. Y(III) is diamagnetic and so the Y(III)-versions of the agents verify that any changes in relaxivity observed are not due to the modification of the nanoparticle but due to the presence and interaction of the Gd(III)-chelate and SPM nanoparticle.

General Information for Examples 4-16

Abbreviations: DMF=dimethylformamide, TFA=trifluoroacetic acid, MeCN=acetonitrile, TIS=triisopropylsilane, fmoc=9-fluorenylmethoxycarbonyl, Boc=tert-butoxycarbonyl, HATU=o-(7-azabenzotriazol-1-yl)-N,N,N',N'-tetramethyluronium hexafluorophosphate, DIPEA=N,N-diisopropylethylamine, DTPA=diethylenetriaminepentaacetic acid, HPLC=high performance liquid chromatography, RP-HPLC=reverse phase high performance liquid chromatography, PDA=photodiode array, ESI-MS=electrospray ionization mass spectrometry, MALDI-TOF MS=matrix assisted laser desorption ionization time of flight mass spectrometry, CHCA=α-cyano-4-hydroxycinnamic acid.

Chemicals: Amino acids were purchased (NovaBiochem, San Diego, Calif.) with the amino functionality fmoc protected and were used as received. Tryptophan was purchased with the side chain Boc protected. All other chemicals and solvents were purchased (Sigma Aldrich, St Louis, Mo.) and used as received.

Instrumentation: UV/visible spectra for the Kaiser test were performed on an Agilent 8453 VV/vis spectrophotometer. ESI-MS was performed on a Varian Quadrupole 1200L. Samples were dissolved in MeOH, 0.22 um filtered, and injected using a syringe pump operating at 50 uL/min. MALDI-TOF MS was performed on a PerkinElmer Voyager DE Pro operating in reflector mode using CHCA as a matrix. Aqueous samples (1 uL) were spotted on a stainless steel plate along with matrix solution (1 uL of saturated CHCA solution in 1:1 MeCN: 0 1% TFA). Samples were allowed to dry under ambient conditions before acquiring spectra. Analytical HPLC-MS was performed on a reverse-phase C$_{18}$ Atlantis T3 column (Waters, T3 5 um, 4.6×250 mm) with a Varian Prostar 363 fluorescence detector, a Varian Prostar PDA 330 UV/vis detector, and a Varian Quadrupole 1200L MS to determine the appropriate gradients to be used for preparative HPLC. Preparative HPLC was performed on a reverse-phase C$_{18}$ Atlantis T3 column (Waters, T3 10 um, 19×250 mm with 19×10 mm guard) with a HewlettPackard 1046A fluorescence detector and a Varian Prostar UV/vis dual wavelength Detector.

Other: All water used was purified using a Milli-Q (Millipore Billerica, Mass.) purification system. Millipore Millex-GN 0.22 um Nylon filters were used for aqueous solutions and Millipore Millex-FG 0.22 um hydrophobic PTFE filters were used for non-aqueous solutions.

Kaiser Test: The Kaiser Test for free amines was used to determine reaction completeness during solid-phase peptide synthesis.

All of the above references are incorporated by reference in their entireties.

We claim:

1. A magnetic resonance contrast agent composition comprising one or more $T_1$ contrast agent portions, and one or more $T_2$ contrast agent portions, wherein said one or more $T_1$ contrast agent portions comprise a paramagnetic metal ion chelate, and wherein said one or more $T_2$ contrast agent portions comprise a cobalt ferrite nanoparticle coated with a SiO$_2$ shell.

2. The magnetic resonance contrast agent composition of claim 1, further comprising one or more linker regions.

3. The magnetic resonance contrast agent composition of claim 1, wherein said paramagnetic metal ion is Gd(III).

4. The magnetic resonance contrast agent composition of claim 2, wherein said linker region is a cleavable linker region.

5. The magnetic resonance contrast agent composition of claim 4, wherein said cleavable linker region comprises a peptide linker portion.

6. The magnetic resonance contrast agent composition of claim 5, wherein said peptide linker portion comprises a MMP-7 peptide linker.

7. The magnetic resonance contrast agent composition of claim 2, wherein said linker region connects one said $T_1$ contrast agent portion to one said $T_2$ contrast agent.

8. The magnetic resonance contrast agent composition of claim 2, wherein a $T_2$ contrast agent portion is connected to more than one $T_1$-relaxation contrast agent portions by multiple linkers.

9. The magnetic resonance contrast agent composition of claim 1, wherein more than one $T_2$ contrast agent portions are connected to more than one $T_1$ contrast agent portions by multiple linkers.

10. The magnetic resonance contrast agent composition of claim 1, further comprising an imaging tag.

11. The magnetic resonance contrast agent composition of claim 10, wherein said imaging tag is and optical imaging tag.

12. The magnetic resonance contrast agent composition of claim 1, further comprising a targeting moiety.

13. A pharmaceutical formulation comprising a contrast agent of claim 1 and a pharmaceutically acceptable carrier, wherein the formulation is suitable for administration as an imaging enhancing agent and the contrast agent is present in an amount sufficient to enhance a magnetic resonance image.

14. A method of generating an image of at least a part of a subject comprising administering the composition of claim 1 to a subject, and generating an image of at least a part of said subject to which said composition has distributed.

* * * * *